United States Patent
Sun

(10) Patent No.: US 10,017,497 B2
(45) Date of Patent: Jul. 10, 2018

(54) PYRROLIDINE GPR40 MODULATORS FOR THE TREATMENT OF DISEASES SUCH AS DIABETES

(71) Applicant: BRISTOL-MYERS SQUIBB COMPANY, Princeton, NJ (US)

(72) Inventor: Chongqing Sun, East Windsor, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/308,428

(22) PCT Filed: May 6, 2015

(86) PCT No.: PCT/US2015/029422
§ 371 (c)(1),
(2) Date: Nov. 2, 2016

(87) PCT Pub. No.: WO2015/171733
PCT Pub. Date: Nov. 12, 2015

(65) Prior Publication Data
US 2017/0217930 A1    Aug. 3, 2017

Related U.S. Application Data

(60) Provisional application No. 61/989,560, filed on May 7, 2014.

(51) Int. Cl.
*C07D 401/14* (2006.01)
*A61K 31/497* (2006.01)
*A61K 45/06* (2006.01)

(52) U.S. Cl.
CPC .......... *C07D 401/14* (2013.01); *A61K 31/497* (2013.01); *A61K 45/06* (2013.01)

(58) Field of Classification Search
None
See application file for complete search history.

(56) References Cited

FOREIGN PATENT DOCUMENTS

| WO | WO2005/012249 A2 | 2/2005 |
| WO | WO2011/044073 A1 | 4/2011 |
| WO | WO2014/078609 A1 | 5/2014 |

OTHER PUBLICATIONS

Sharma, N. Mini Rev. Med. Chem. 2017; 17(11) 947-958.*
UCSF Medical Center. Neurological Disorders. (2016) Web: <https://www.ucsfhealth.org/conditions/neurological_disorders/>.*
MayoClinic. Diabetes prevention: 5 tips for taking control. (2016) Web: <http://www.mayoclinic.org/diseases-conditions/type-2-diabetes/in-depth/diabetes-prevention/art-20047639>.*
Simpkins, L. et al., "Potent non-nitrile dipeptidic dipeptidyl peptidase IV inhibitors", Bioorganic & Medicinal Chemistry Letters, vol. 17, pp. 6476-6480 (2007).

* cited by examiner

*Primary Examiner* — Deepak R Rao
*Assistant Examiner* — Laura M Daniel
(74) *Attorney, Agent, or Firm* — Yong Lu; Barry H. Jacobsen

(57) ABSTRACT

The present invention provides compounds of Formula (I) or a stereoisomer, a tautomer, a pharmaceutically acceptable salt, or a solvate thereof, wherein all of the variables are as defined herein. These compounds are GPR40 G protein-coupled receptor modulators which may be used as medicaments.

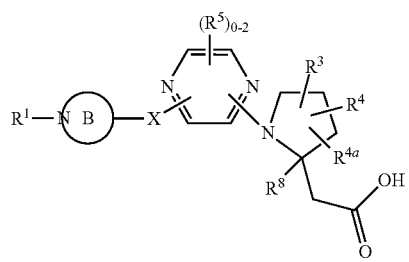

18 Claims, No Drawings

PYRROLIDINE GPR40 MODULATORS FOR THE TREATMENT OF DISEASES SUCH AS DIABETES

CROSS-REFERENCE TO RELATED APPLICATIONS

This application is a national phase application under 35 U.S.C. § 371 of International Patent Application No. PCT/US2015/029422, filed May 6, 2015, which claims priority to U.S. Provisional Application Ser. No. 61/989,560, filed May 7, 2014, the entire content of which is incorporated herein by reference.

FIELD OF THE INVENTION

The present invention provides novel carboxylic acid substituted pyrrolidine compounds, and their analogues thereof, which are GPR40 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. GPR40 is also expressed in enteroendocrine cells wherein activation promotes the secretion of gut incretin hormones, such as GLP-1, GIP, CCK and PYY. To decrease medical burden of type 2 diabetes through enhanced glycemic control, GPR40 modulator compounds hold the promise of exerting an incretin effect to promote GSIS as well as potential combination with a broad range of anti-diabetic drugs.

The present invention relates to novel substituted pyrrolidine compounds which have the ability to modulate GPR40. Such compounds are therefore potentially useful for the treatment of diabetes and related conditions.

SUMMARY OF THE INVENTION

The present invention provides substituted pyrrolidine compounds, and their analogues thereof, which are useful as GPR40 modulators, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The present invention also provides a crystalline form of one of the compounds of the present invention or stereoisomers, tautomers, pharmaceutically acceptable salts, polymorphs, or solvates thereof.

The compounds of the invention may be used in the treatment of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

or a stereoisomer, a tautomer, a pharmaceutically acceptable salt, a polymorph, or a solvate thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, $-(CH_2)_m-C_{3-6}$ carbocycle substituted with 0-1 $R^{12}$, and $-(CH_2)_m$-(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, OH, $CO_2H$, $C_{1-6}$ alkyl substituted with 0-1 $R^{10}$, $C_{2-6}$ alkenyl substituted with 0-1 $R^{10}$, $C_{2-6}$ alkynyl substituted with 0-1 $R^{10}$, $C_{1-4}$ haloalkyl substituted with 0-1 $R^{10}$, $C_{1-6}$ haloalkoxy substituted with 0-1 $R^{10}$, $-O(CH_2)_{1-2}O(CH_2)_{1-4}R^{10}$, $OR^9$, $SR^9$, $C(O)OR^9$, $CO_2R^9$, $S(O)R^9$, $SO_2R^9$, $CONHR^9$, $-(O)_n-(CH_2)_m$-(phenyl substituted with 0-2 $R^{10}$), and $-(O)_n-(CH_2)_m$-(5- to 10-membered heteroaryl containing carbon atoms and 1-4 heteroatoms selected from N, $NR^{11}$, O, and S; wherein said heteroaryl is substituted with 0-2 $R^{10}$);

$R^4$ and $R^{4a}$ are independently selected from: H, halogen, $C_{1-6}$ alkyl, $C_{1-6}$ alkoxy, and $-(CH_2)_m-C_{3-6}$ carbocycle;

$R^5$, at each occurrence, is independently selected from: halogen, $C_{1-6}$ alkyl, $C_{1-6}$ alkoxy, $C_{1-6}$ haloalkyl, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, $-(O)_n-(CH_2)_m-(C_{3-10}$ carbocycle substituted with 0-2 $R^7$), and $-(CH_2)_m$-(5- to 10-membered heteroaryl containing carbon atoms and 1-4 heteroatoms selected from N, $NR^{11}$, O, and S); wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^8$ is independently selected from: H and $C_{1-4}$ alkyl;

$R^9$, at each occurrence, is independently selected from: $C_{1-6}$ alkyl substituted with substituted with 0-1 $R^{10}$, and $C_{1-4}$ haloalkyl substituted with 0-1 $R^{10}$;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and n, at each occurrence, is independently 0 or 1.

In a second aspect, the present disclosure provides a compound of Formula (I), wherein $R^4$ is hydrogen and $R^8$ is hydrogen, further characterized by Formula (II):

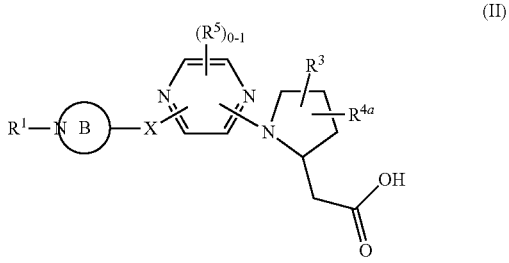

(II)

or a stereoisomer, a tautomer, a pharmaceutically acceptable salt, a polymorph, or a solvate thereof, wherein:

X is independently selected from: O, $N(CH_3)$, $CH_2$, $CH_2O$, and $CH_2CH_2O$;

ring B is independently a 4- to 7-membered saturated heterocycle containing carbon atoms and the nitrogen atom shown in ring B; and ring B is substituted with 0-4 $R^2$;

$R^1$ is independently phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl substituted with 0-1 $R^{12}$, $C_{1-4}$ alkoxy substituted with 0-1 $R^{12}$, $C_{1-4}$ haloalkyl, $C_{1-4}$ haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: $C_{1-6}$ alkyl substituted with 0-1 $R^{10}$, $C_{1-6}$ alkoxy substituted with 0-1 $R^{10}$, $C_{1-4}$ haloalkyl substituted with 0-1 $R^{10}$, and $C_{1-4}$ haloalkoxy substituted with 0-1 $R^{10}$, and $-O(CH_2)_{1-2}O(CH_2)_{1-4}R^{10}$;

$R^{4a}$ is independently selected from: H, halogen, $C_{1-4}$ alkyl, $C_{1-4}$ alkoxy, and $-(CH_2)_m-C_{3-6}$ carbocycle;

$R^5$, at each occurrence, is independently selected from: halogen, $C_{1-6}$ alkyl, $C_{1-6}$ haloalkyl, $C_{1-6}$ alkoxy, and $C_{1-6}$ haloalkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-4}$ alkoxy substituted with 0-1 $R^7$, $-(O)_n-(CH_2)_m-(C_{3-6}$ carbocycle substituted with 0-2 $R^7$), $-(CH_2)_m$-(naphthyl substituted with 0-2 $R^7$), and $-(CH_2)_m$-(5- to 10-membered heteroaryl containing carbon atoms and 1-4 heteroatoms selected from N, O, and S; wherein said heteroaryl is substituted with 0-2 $R^7$);

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^{10}$, at each occurrence, is independently selected from: CN, $C_{1-4}$ alkoxy, $C_{1-4}$ haloalkoxy, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^{12}$, at each occurrence, is independently selected from: halogen, CN, $C_{1-4}$ alkyl, $C_{1-4}$ alkoxy, $C_{1-4}$ haloalkyl, $C_{1-4}$ haloalkoxy, $CO_2(C_{1-4}$ alkyl), and tetrazolyl;

m, at each occurrence, is independently 0, 1, or 2; and n, at each occurrence, is independently 0 or 1.

In a third aspect, the present disclosure includes a compound of Formula (I) or (II), or a stereoisomer, a tautomer, a pharmaceutically acceptable salt, a polymorph, or a solvate thereof, within the scope of the first or second aspect, wherein:

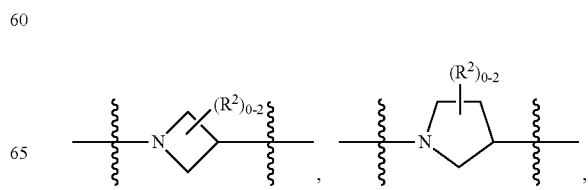

-continued

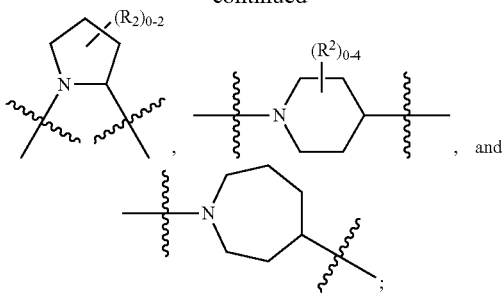

ring B is independently selected from:

R¹ is independently phenyl substituted with 0-3 R⁶ or a heteroaryl substituted with 0-2 R⁶; wherein said heteroaryl is selected from: furanyl, oxazolyl, thiazolyl, pyrazolyl, oxadiazolyl, pyridinyl, pyrimidinyl, and pyrazinyl;

R², at each occurrence, is independently selected from: OH, halogen, $C_{1-4}$ alkyl substituted with 0-1 CN, $C_{1-4}$ alkoxy, benzyl, and tetrazolylmethyl;

R³ is independently selected from: $C_{1-4}$ alkyl substituted with 0-1 R¹⁰, $C_{1-4}$ alkoxy substituted with 0-1 R¹⁰, $C_{1-4}$ haloalkyl substituted with 0-1 R¹⁰, and $C_{1-4}$ haloalkoxy substituted with 0-1 R¹⁰;

R⁴ᵃ is independently selected from: H, halogen $C_{1-4}$ alkyl, $C_{1-4}$ alkoxy, and $C_{3-6}$ cycloalkyl;

R⁶, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl; and R¹⁰, at each occurrence, is independently selected from: CN, $C_{1-4}$ alkoxy, $C_{1-4}$ haloalkoxy, $CO_2(C_{1-4}$ alkyl), and tetrazolyl.

In a fourth aspect, the present disclosure includes a compound of Formula (I) or (II), or a stereoisomer, a tautomer, a pharmaceutically acceptable salt, a polymorph, or a solvate thereof, within the scope of any of the above aspect, wherein:

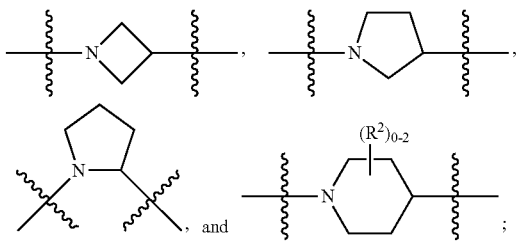

ring B is independently selected from:

R¹, at each occurrence, is independently phenyl substituted with 0-3 R⁶, pyridinyl substituted with 0-2 R⁶, pyrazinyl substituted with 0-2 R⁶, pyrimidinyl substituted with 0-2 R⁶, or thiazolyl substituted with 0-2 R⁶; and R², at each occurrence, is independently selected from: halogen, $C_{1-4}$ alkyl, $C_{1-4}$ alkoxy and tetrazolylmethyl.

In a fifth aspect, the present disclosure includes a compound of Formula (I) or (II), or a stereoisomer, a tautomer, a pharmaceutically acceptable salt, a polymorph, or a solvate thereof, within the scope of any of the above aspect, wherein:

R¹, at each occurrence, is independently phenyl substituted with 0-3 R⁶ or pyridinyl substituted with 0-2 R⁶;

R³, at each occurrence, is independently selected from: $C_{1-4}$ alkyl substituted with 0-1 $C_{1-4}$ alkoxy, $C_{1-4}$ alkoxy substituted with 0-1 $C_{1-4}$ alkoxy, and $C_{1-4}$ haloalkyl; and R⁶, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl.

In a sixth aspect, the present disclosure includes a compound of Formula (III) or (IIIa):

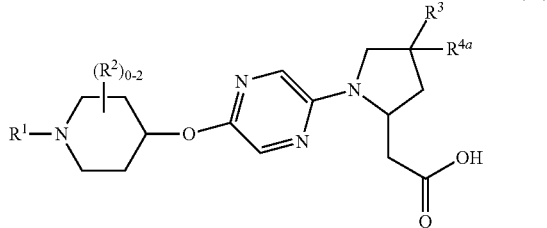

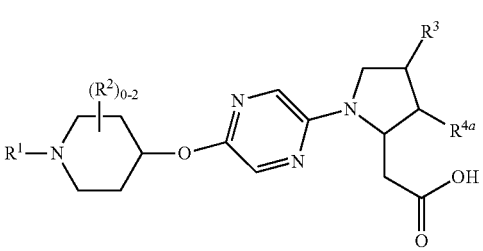

or a stereoisomer, a tautomer, a pharmaceutically acceptable salt, a polymorph, or a solvate thereof, wherein:

R¹, at each occurrence, is independently phenyl substituted with 0-3 R⁶ or pyridinyl substituted with 0-2 R⁶;

R², at each occurrence, is independently selected from: halogen, $C_{1-4}$ alkyl, and $C_{1-4}$ alkoxy;

R³, at each occurrence, is independently: $C_{1-4}$ alkyl substituted with 0-1 $C_{1-4}$ alkoxy, $C_{1-4}$ alkoxy substituted with 0-1 $C_{1-4}$ alkoxy, and $C_{1-4}$ haloalkyl;

R⁴ᵃ, at each occurrence, is independently selected from: H, halogen, $C_{1-4}$ alkyl, $C_{1-4}$ alkoxy, and cyclopropyl;

R⁵, at each occurrence, is independently selected from: halogen, $C_{1-4}$ haloalkyl, and $C_{1-6}$ alkoxy; and R⁶, at each occurrence, is independently selected from: halogen, $C_{1-6}$ alkyl, $C_{1-4}$ alkoxy, $C_{3-6}$ cycloalkyl substituted with 0-2 $C_{1-4}$ alkyl, and $C_{5-6}$ cycloalkenyl substituted with 0-2 $C_{1-4}$ alkyl.

In a seventh aspect, the present invention provides a compound selected from the exemplified examples or a stereoisomer, a tautomer, a pharmaceutically acceptable salt, a polymorph, or a solvate thereof.

In another aspect, the present invention provides a compound selected from any subset list of compounds or a single compound from the exemplified examples within the scope of any of the above aspects.

In another embodiment, the compounds of the present invention have hGPR40 EC₅₀ values≤5 μM.

In another embodiment, the compounds of the present invention have hGPR40 EC₅₀ values≤1 μM.

In another embodiment, the compounds of the present invention have hGPR40 EC₅₀ values≤0.5 μM.

In another embodiment, the compounds of the present invention have hGPR40 EC₅₀ values≤0.2 μM.

In another embodiment, the compounds of the present invention have hGPR40 $EC_{50}$ values≤0.1 μM.

II. Other Embodiments of the Invention

Additional embodiments of the invention include compounds having the structure:

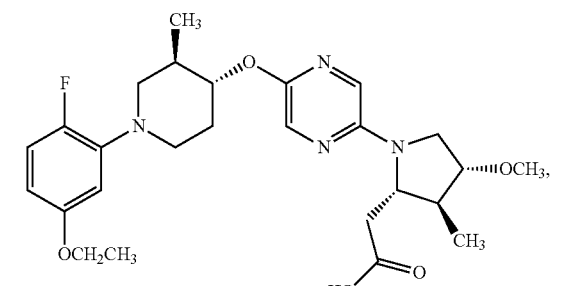

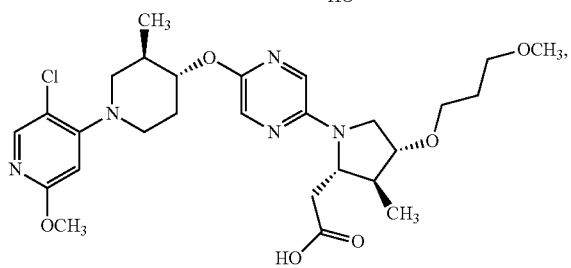

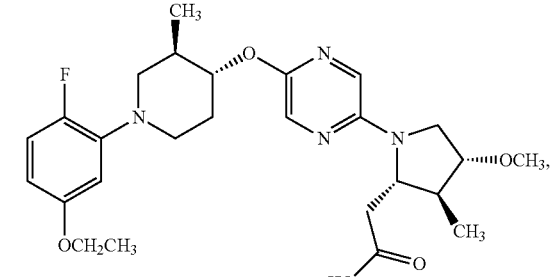

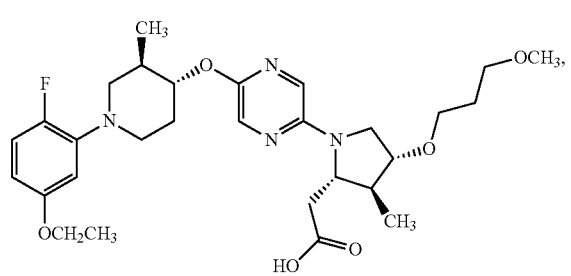

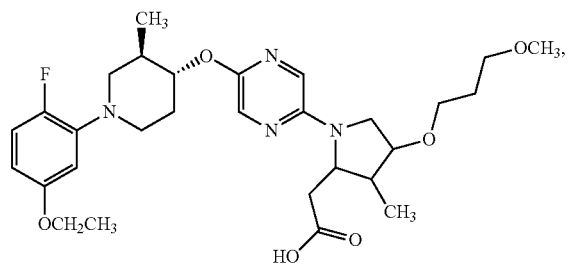

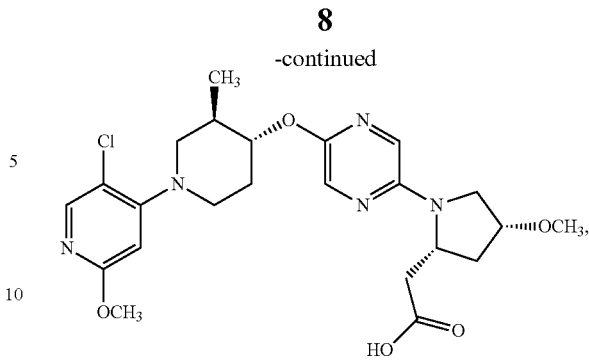

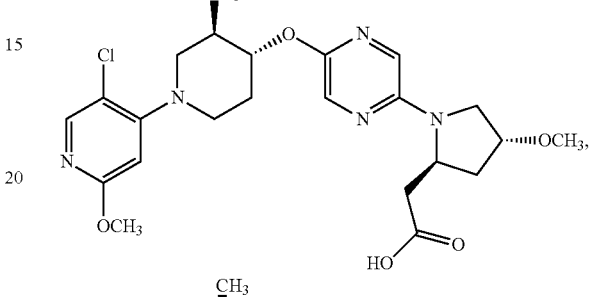

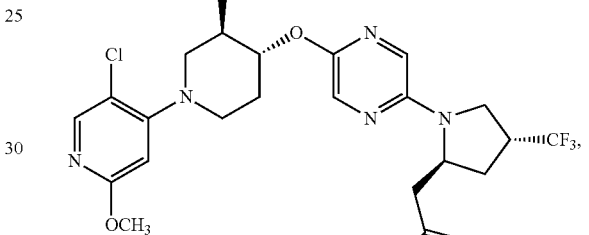

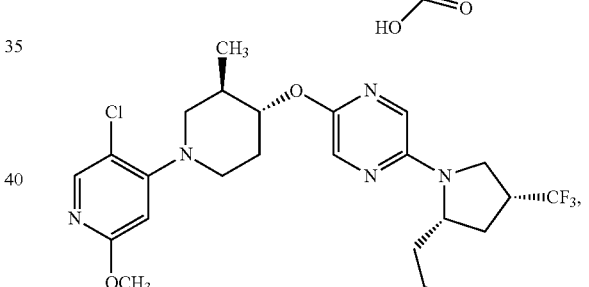

or a stereoisomer, a tautomer, a pharmaceutically acceptable salt, a polymorph, or a solvate thereof.

Another embodiment of the invention provides a compound having the structure:

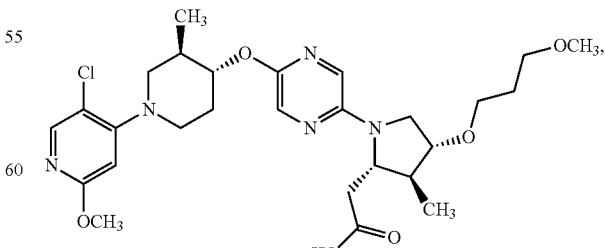

or a stereoisomer, a tautomer, a pharmaceutically acceptable salt, a polymorph, or a solvate thereof.

Another embodiment of the invention provides a compound having the structure:

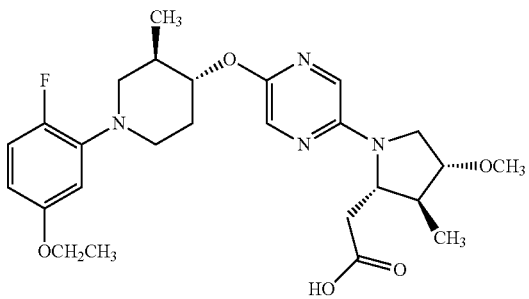 [SMILES: CCOc1ccc(F)c(N2CC[C@@H](Oc3cnc(N4C[C@H](OC)[C@@H](C)[C@@H]4CC(=O)O)cn3)[C@H](C)C2)c1]

or a stereoisomer, a tautomer, a pharmaceutically acceptable salt, a polymorph, or a solvate thereof.

Another embodiment of the invention provides a compound having the structure:

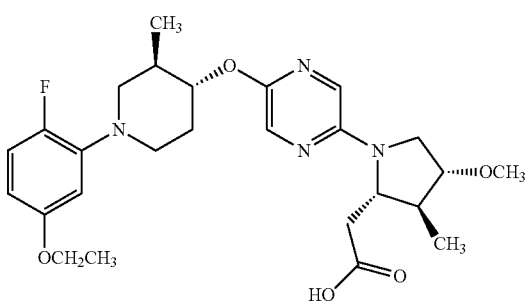 [SMILES: CCOc1ccc(F)c(N2CC[C@@H](Oc3cnc(N4C[C@H](OC)[C@@H](C)[C@@H]4CC(=O)O)cn3)[C@H](C)C2)c1]

or a stereoisomer, a tautomer, a pharmaceutically acceptable salt, a polymorph, or a solvate thereof.

Another embodiment of the invention provides a compound having the structure:

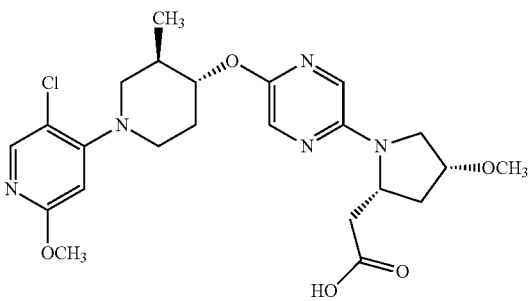 [SMILES: COc1cc(N2CC[C@@H](Oc3cnc(N4C[C@H](OC)C[C@@H]4CC(=O)O)cn3)[C@H](C)C2)c(Cl)cn1]

or a stereoisomer, a tautomer, a pharmaceutically acceptable salt, a polymorph, or a solvate thereof.

Another embodiment of the invention provides a compound having the structure:

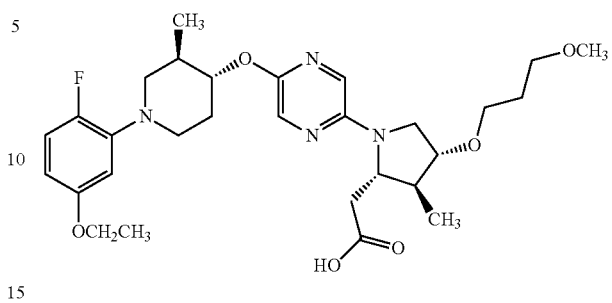

or a stereoisomer, a tautomer, a pharmaceutically acceptable salt, a polymorph, or a solvate thereof.

Another embodiment of the invention provides a compound having the structure:

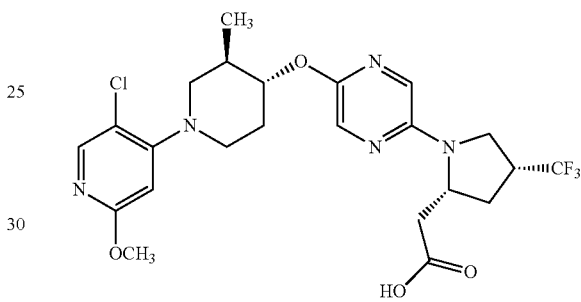

or a stereoisomer, a tautomer, a pharmaceutically acceptable salt, a polymorph, or a solvate thereof.

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, a polymorph, or a solvate thereof.

In another embodiment, the present invention provides a process for making a compound of the present invention or a stereoisomer, a tautomer, a pharmaceutically acceptable salt, a polymorph, or a solvate thereof.

In another embodiment, the present invention provides an intermediate for making a compound of the present invention or a stereoisomer, a tautomer, a pharmaceutically acceptable salt, a polymorph, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin, alogliptin, and "BMS DPP4i"), and/or a sodium-glucose transporter-2 (SGLT2) inhibitor (for example a member selected from dapagliflozin, canagliflozin, empagliflozin and remagliflozin).

In a preferred embodiment, the present invention provides pharmaceutical composition, wherein the additional therapeutic agents are, for example, a DPP4 inhibitor (for example a member selected from saxagliptin, sitagliptin, vildagliptin, linagliptin, alogliptin, and "BMS DPP4i").

In a preferred embodiment, the present invention provides pharmaceutical composition, wherein the additional therapeutic agents are, for example, an SGLT2 inhibitor (for example a member selected from dapagliflozin, canagliflozin, empagliflozin and remagliflozin).

In another embodiment, the present invention provides a method for the treatment of multiple diseases or disorders associated with GPR40, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, and liver diseases such as NASH (Non-Alcoholic SteatoHepatitis), NAFLD (Non-Alcoholic Fatty Liver Disease), liver cirrhosis, inflammatory bowel diseases incorporating ulcerative colitis and Crohn's disease, celiac disease, osteoarthritis, nephritis, psoriasis, atopic dermatitis, and skin inflammation.

In another embodiment, the present invention provides a method for the treatment of diabetes, hyperglycemia, gestational diabetes, obesity, dyslipidemia, hypertension and cognitive impairment, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of cognitive impairment, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR40.

In another embodiment, the present invention also provides the use of a compound of the present invention for the manufacture of a medicament for the treatment of multiple diseases or disorders associated with GPR40.

In another embodiment, the present invention provides a method for the treatment of multiple diseases or disorders associated with GPR40, comprising administering to a patient in need thereof a therapeutically effective amount of a first and second therapeutic agent, wherein the first therapeutic agent is a compound of the present invention. Preferably, the second therapeutic agent, for example, a DPP4 inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR40.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR40 receptor modulator of the present invention include, but are not limited to, insulin secretagogues or insulin sensitizers, other GPR40 receptor modulators, or other antidiabetic agents. These agents include, but are not limited to, DPP4 inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR119 receptor modulators (for example, MBX-2952, PSN821, and APD597), GPR120 receptor modulators (for example, as described in Shimpukade, B. et al., *J. Med. Chem.*, 55(9):4511-4515 (2012)), SGLT2 inhibitors (for example, dapagliflozin, canagliflozin, empagliflozin and remagliflozin), MGAT inhibitors (for example, as described in Barlind, J. G. et al., *Bioorg. Med. Chem. Lett.*, 23(9): 2721-2726 (2013)), amylin analogs such as pramlintide, and/or insulin.

The GPR40 receptor modulator of the present invention may also be optionally employed in combination with agents for treating complication of diabetes. These agents include PKC inhibitors and/or AGE inhibitors.

The GPR40 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The GPR40 receptor modulator of the present invention may also be employed in combination with an agonist of the glucagon-like peptide-1 receptor (GLP-1 R), such as exenatide, liraglutide, GLP-1 (1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and butoxy (e.g., n-butoxy, isobutoxy and t-butoxy). Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York, 1997. "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, imidazopyridazinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolopyrimidinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, pyrimidinyl, pyrazinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, imidazolopyridinyl, imidazopyridazinyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, pyrazolopyridinyl and pyrazolopyrimidinyl.

Examples of 5- to 6-membered heterocycles include, but are not limited to, pyridinyl, furanyl, thienyl, pyrrolyl, pyrazolyl, pyrazinyl, piperazinyl, piperidinyl, pyrimidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2-}$)ammonium ($R_nNH_m$+ where n=0–4 and m=0–4) and the like.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, Fourth Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985);

b) Widder, K. et al., eds., *Methods in Enzymology*, 112: 309-396, Academic Press (1985);

c) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);

d) Bundgaard, H., *Adv. Drug Deliv. Rev.*, 8:1-38 (1992);

e) Nielsen, N. M. et al., *J. Pharm. Sci.*, 77:285 (1988);

f) Kakeya, N. et al., *Chem. Pharm. Bull.*, 32:692 (1984); and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H (also represented as 'D' for deuterium) and $^3$H, carbon such as $^{11}$C, $^{13}$C, and $^{14}$C, nitrogen, such as $^{13}$N and $^{15}$N, oxygen, such as $^{15}$O, $^{17}$O, and $^{18}$O. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{15}$O, and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "Å" for "Angstroms", "° C." for degrees Celsius, "eq" for equivalent or equivalents, "g" for gram or grams, "mg" for milligram or milligrams, "L" for liter or liters, "mL or ml" for milliliter or milliliters, "µL" for microliter or microliters, "N" for normal, "M" for molar, "N" for normal, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "RP-Prep. HPLC" for reverse phase preparative HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcCl acetyl chloride
Ac$_2$O acetic anhydride
AcOH acetic acid
ADDP 1,1'-(azodicarbonyl)dipiperidine
Ag$_2$O silver oxide
atm atmosphere
9-BBN 9-borabicyclo[3.3.1]nonane
BF$_3$·OEt$_2$ boron trifluoride diethyl etherate
BF$_3$·SMe$_2$ boron trifluoride dimethyl sulfide
BH$_3$·DMS borane dimethyl sulfide complex
Bn benzyl
Boc tert-butyloxycarbonyl
Boc$_2$O di-tert-butyl dicarbonate
Bu butyl
n-BuOH n-butanol
Bu$_3$P tributylphosphine
CDCl$_3$ deutero-chloroform
CD$_2$Cl$_2$ deutero-dichloromethane
cDNA complimentary DNA
CH$_2$Cl$_2$ or DCM dichloromethane
CH$_3$CN or MeCN acetonitrile
CHCl$_3$ chloroform
CSA camphorsulfonic acid
Cs$_2$CO$_3$ cesium carbonate
Cu(OAc)$_2$ copper(II) acetate
CuI copper(I) iodide
CuBr·SMe$_2$ copper(I) bromide dimethylsulfide complex
DAST (diethylamino)sulfur trifluoride
DBAD di-tert-butyl azodicarboxylate
DEAD diethyl azodicarboxylate
DIAD diisopropyl azodicarboxylate
DIPEA diisopropylethylamine
DMAP 4-(dimethylamino)pyridine
DMF dimethyl formamide
DMSO dimethyl sulfoxide
DtBPF 1,1'-bis(di-tert-butylphosphino)ferrocene
EDTA ethylenediaminetetraacetic acid
Et ethyl
Et$_2$O diethyl ether
EtOAc ethyl acetate
EtOH ethanol
H$_2$ molecular hydrogen
H$_2$O$_2$ hydrogen peroxide
H$_2$SO$_4$ sulfuric acid
HCl hydrochloric acid
Hex hexanes
i-Bu isobutyl
i-Pr isopropyl
i-PrOH or IPA isopropanol
KCN potassium cyanide
K$_2$CO$_3$ potassium carbonate
K$_2$HPO$_4$ dipotassium phosphate
KHSO$_4$ potassium bisulfate
KI potassium iodide KOH potassium hydroxide
KOtBu potassium tert-butoxide
$K_3PO_4$ tripotassium phosphate
LAH lithium aluminum hydride
LDA lithium diisopropylamide
L.G. leaving group
LHMDS lithium hexamethyldisilazide
$LiBH_4$ lithium borohydride
LiOH lithium hydroxide
L-Selectride lithium tri-sec-butylborohydride
Me methyl
MeI iodomethane
MeLi methyl lithium
MeOH methanol
$MgSO_4$ magnesium sulfate
MsCl methanesulfonyl chloride
NaDCC sodium dichloroisocyanurate
NaHMDS sodium hexamethyldisilazide
$NaNO_2$ sodium nitrite
$Na_2SO_4$ sodium sulfate
$Na_2S_2O_3$ sodium thiosulfate
$NaBH_4$ sodium borohydride
NaCl sodium chloride
NaCN sodium cyanide
NCS N-chlorosuccinimide
NaH sodium hydride
$NaHCO_3$ sodium bicarbonate
NaOH sodium hydroxide
NaOtBu sodium tert-butoxide
$NH_3$ ammonia
$NH_4Cl$ ammonium chloride
$NH_4OH$ ammonium hydroxide
$Pd(OAc)_2$ palladium(II) acetate
Pd/C palladium on carbon
$PdCl_2(dppf)$ 1,1'-bis(diphenylphosphino)ferrocene-palladium(II)dichloride
$PdCl_2(dtbpf)$ [1,1'-bis(di-tert-butylphosphino)ferrocene]dichloropalladium(II)
$PdCl_2(PPh_3)_2$ bis(triphenylphosphine)palladium(II) dichloride
$Pd_2(dba)_3$ tris(dibenzylideneacetone)dipalladium(0)
$Pd(Ph_3P)_4$ tetrakis(triphenylphosphine)palladium(0)
P.G. protecting group
Ph phenyl
$Ph_3P$ triphenylphosphine
Pr propyl
PS polystyrene
$PtO_2$ platinum(IV) oxide
SFC supercritical fluid chromatography
$SiO_2$ silica oxide
SPhos 2-dicyclohexylphosphino-2',6'-dimethoxy-1,1'-biphenyl
SPhos precatalyst chloro(2-dicyclohexylphosphino-2',6'-dimethoxy-1,1'-biphenyl) [2-(2-aminoethylphenyl)]palladium(II)-methyl-t-butyl ether adduct
TBAF tetrabutylammonium fluoride
t-Bu tert-butyl
TBDPS-Cl tert-butylchlorodiphenylsilane
TBS-Cl tert-butyldimethylsilyl chloride
TBSOTf tert-butyldimethylsilyl trifluoromethanesulfonate
TCCA trichloroisocyanuric acid
TEA or $NEt_3$ triethylamine
TEMPO 2,2,6,6-tetramethyl-1-piperidinyloxy
TFA trifluoroacetic acid
$Tf_2O$ trifluoromethanesulfonic anhydride
THF tetrahydrofuran
TMS-Cl chlorotrimethylsilane
TsCl 4-methylbenzene-1-sulfonyl chloride
TsOH or pTsOH para-toluenesulfonic acid
XPhos 2-dicyclohexylphosphino-2',4',6'-triisopropylbiphenyl The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*, Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

Methods for synthesis of a large variety of substituted pyrrolidine compounds useful as starting materials for the preparation of compounds of the present invention are well known in the art. For examples of methods useful for the preparation of pyrrolidine materials see the following references and citations therein: Katritzky et al., eds., *Comprehensive Heterocyclic Chemistry*, Pergamon Press Inc., New York (1996); Bellina, F. et al., *Tetrahedron*, 62:7213 (2006); Wolfe, J. P., *Eur. J. Org. Chem.*, 571 (2007); Deng, Q.-H. et al., *Organic Letters*, 10:1529 (2008); Pisaneschi, F. et al., *Synlett*, 18:2882 (2007); Najera, C. et al., *Angewandte*

Chemie, International Edition, 44(39):6272 (2005); Sasaki, N. A., Methods in Molecular Medicine, 23(Peptidomimetics Protocols):489 (1999); Zhou, J.-Q. et al., Journal of Organic Chemistry, 57(12):3328 (1992); Coldham, I. et al., Tetrahedron Letters, 38(43):7621 (1997); Schlummer, B. et al., Organic Letters, 4(9):1471 (2002); Larock, R. C. et al., Journal of Organic Chemistry, 59(15):4172 (1994); Galliford, C. V. et al., Organic Letters, 5(19):3487 (2003); Kimura, M. et al., Angewandte Chemie, International Edition, 47(31):5803 (2008); Ney, J. E. et al., Adv. Synth. Catal., 347:1614 (2005); Paderes, M. C. et al., Organic Letters, 11(9):1915 (2009); Wang, Y.-G. et al., Organic Letters, 11(9):2027 (2009); Cordero, F. M. et al., Journal of Organic Chemistry, 74(11):4225 (2009); Hoang, C. T. et al., Journal of Organic Chemistry, 74(11):4177 (2009). Luly, J. R. et al., Journal of the American Chemical Society, 105:2859 (1983); Kimball, F. S. et al., Bioorganic and Medicinal Chemistry, 16:4367 (2008); Bertrand, M. B. et al., Journal of Organic Chemistry, 73(22):8851 (2008); Browning, R. G. et al., Tetrahedron, 60:359 (2004); Ray, J. K. et al., Bioorganic and Medicinal Chemistry, 2(12):1417 (1994); Evans, G. L. et al., Journal of the American Chemical Society, 72:2727 (1950); Stephens, B. E. et al., Journal of Organic Chemistry, 74(1):254 (2009); Spangenberg, T. et al., Organic Letters, 11(2):261 (2008); and Qiu, X.-L. et al., Journal of Organic Chemistry, 67(20):7162 (2008).

Compounds of Formula (I) may be synthesized starting with substituted pyrazine D ($LG^1$ may be equal or not equal to $LG^2$) via coupling to alcohol C using a base, e.g., NaH, to give intermediate E as depicted in Scheme 1. Alcohol C can be prepared by displacement of LG in intermediate A via amine B using S-Phos precatalyst and a base, such as LiHMDS, or optionally via uncatalyzed displacement of LG in intermediate A. Intermediate G may be synthesized via coupling pyrrolidine F to intermediate E using a palladium catalyst, e.g., Pd(OAc)$_2$, a phosphine ligand, such as 1,1'-bis(di-tert-butylphosphino)ferrocene in the presence of a base, e.g., sodium tert-butoxide. The cyano group in intermediate G can be converted to a methyl ester via an acid, e.g., hydrochloric acid in the presence of methanol, then hydrolyzed via LiOH, or directly hydrolyzed via KOH to provide compounds of Formula (I).

Scheme 1

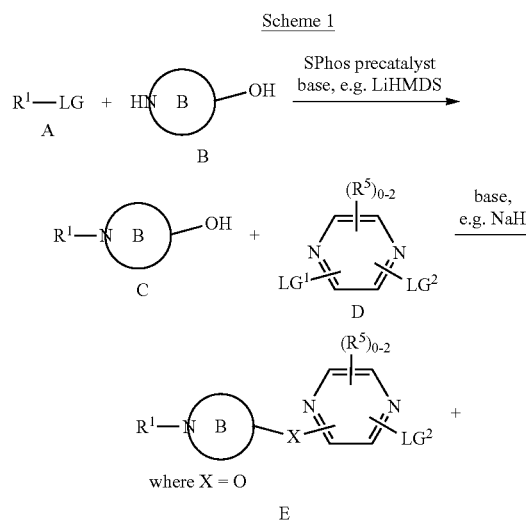

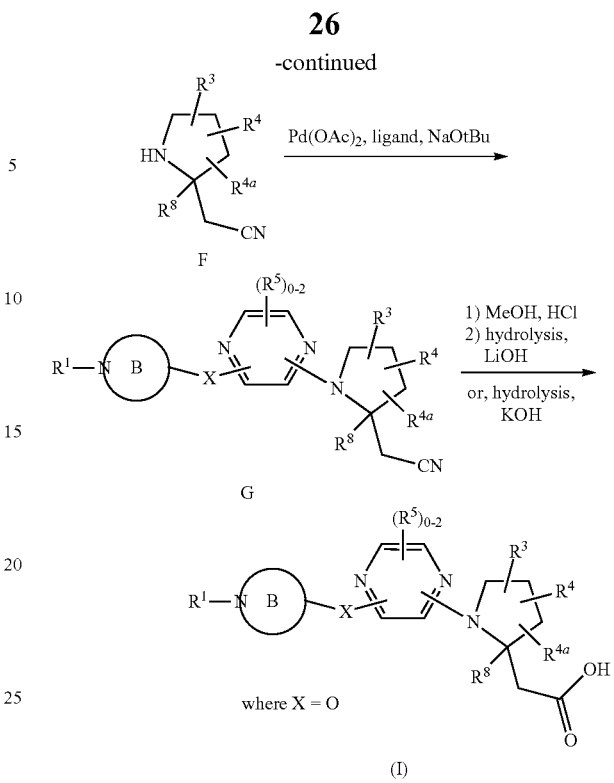

Intermediate F can be synthesized by activation of N-protected pyrrolidinol H via methanesulfonyl chloride and a base, for example Et$_3$N, and displacement with sodium cyanide to nitrile I. Removal of P. G. on intermediate I, such as hydrogenolysis (when P. G. is a Cbz group) or acid-catalyzed hydrolysis (when P. G. is a Boc group) to provide intermediate F.

Scheme 2

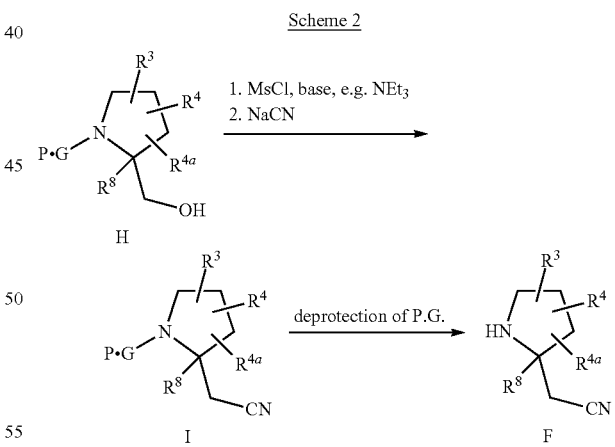

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from β cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^{2+}]_i$ in β cells and subsequent stimulation of insulin secretion (Itoh et al., Nature, 422:173-176 (2003)). Selective small molecule agonists of GPR40 have been shown to promote GSIS and reduce blood glucose in mice (Tan et al., Diabetes, 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., Diabetes, 57:2280-2287 (2008) Luo et al., PLoS ONE, 7:1-12 (2012)). Fatty acids are also known to play a role in neuronal development and function, and GPR40 has been reported as a potential modulator of the fatty acid effects on neurons (Yamashima, T., Progress in Neurobiology, 84:105-115 (2008)).

Given the increase in the worldwide patient population afflicted by type 2 diabetes, there is a need for novel therapies which are effective with minimal adverse events. To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

In Vitro GPR40 Assays

FDSS-Based Intracellular Calcium Assay

Cell lines expressing GPR40 are generated using the pDEST-3×FLAG gene expression system and are cultured in culture medium comprising the following components: F12 (Gibco #11765), 10% lipid deprived fetal bovine serum, 250 µg/mL zeocin and 500 µg/mL G418. To conduct the fluorescent imaging plate reader (FLIPR)-based calcium flux assay to measure intracellular $Ca^{2+}$ response, cells expressing GPR40 are plated on 384 well plates (BD Biocoat #356697) at a density of 20,000 cells/20 µL medium per well in phenol red and serum-free DMEM (Gibco #21063-029) and incubated overnight. Using BD kit #s 80500-310 or -301, the cells are incubated with 20 µL per well of Hank's buffered salt solution with 1.7 mM probenecid and Fluo-3 at 37° C. for 30 min. Compounds are dissolved in DMSO and diluted to desired concentrations with assay buffer and added to the cells as 3× solution (20 µL per well). Run fluorescence/luminescence reader FDSS (Hamamatsu) to read intracellular $Ca^{2+}$ response.

The exemplified Examples disclosed below were tested in the Human GRP40 In Vitro assay described above and found having hGRP40 modulating activity, reported as hGPR40 $EC_{50}$.

GPR40 IP-One HTRF Assays in HEK293/GPR40 Inducible Cell Lines

Human, mouse and rat GPR40-mediated intracellular IP-One HTRF assays were established using human embryonic kidney HEK293 cells stably transfected with a tetracycline-inducible human, mouse or rat GPR40 receptor. Cells were routinely cultured in growth medium containing DMEM (Gibco Cat. #12430-047), 10% qualified FBS (Sigma, Cat. #F2442), 200 µg/mL hygromycin (Invitrogen, Cat. #16087-010) and 1.5 µg/mL blasticidin (Invitrogen, Cat. #R210-01). About 12-15 million cells were passed into a T175 tissue culture flask (BD Falcon 353112) with growth medium and incubated for 16-18 hours (overnight) at 37° C. with 5% $CO_2$. The next day, assay medium was exchanged with growth medium containing 1000 ng/mL of tetracycline (Fluka Analytical, Cat. #87128) to induce GPR40 expression for 18-24 hours at 37° C. incubator with 5% $CO_2$. After induction, the cells were washed with PBS (Gibco, Cat. #14190-036) and detached with Cell Stripper (Cellgro, Cat. #25-056-CL). 10-20 mL growth medium were added to the flask and cells were collected in 50 mL tubes (Falcon, Cat. #352098) and spun at 1000 RPM for 5 minutes. Culture medium was aspirated and the cells were resuspended in 10 mL of 1× IP-One Stimulation Buffer from the Cisbio IP-One kit (Cisbio, Cat. #62IPAPEJ). The cells were diluted to 1.4×106 cells/mL in Stimulation Buffer.

Test compounds were 3-fold, 11-point serially diluted in DMSO in a REMP assay plate (Matrix Cat. #4307) by Biocel (Agilent). The compounds were transferred into an Echo plate (Labcyte, Cat. #LP-0200) and 20 nL of diluted compounds were transferred to an assay plate (proxi-plate from Perkin Elmer, Cat. #6008289) by Echo acoustic nano dispenser (Labcyte, model ECHO550). 14 µL of the diluted cells were then added to the assay plate by Thermo (SN 836 330) Combi Drop and incubated at room temperature for 45 minutes. Then 3 µL of IP1 coupled to dye D2 from the Cisbio IP-One kit were added to the assay plate followed by 3 µL of Lumi4-Tb cryptate K from the kit. The plate was further incubated at room for 1 hour before reading on the Envision (Perkin Elmer Mode12101) with an HTRF protocol. Activation data for the test compound over a range of concentrations was plotted as percentage activation of the test compound (100%=maximum response). After correcting for background [(sample read-mean of low control)/(mean of high control-mean of low control)](low control is DMSO without any compound), $EC_{50}$ values were determined. The $EC_{50}$ is defined as the concentration of test compound which produces 50% of the maximal response and was quantified using the 4 parameter logistic equation to fit the data. The maximal Y value observed (% Ymax) was calculated relative to a BMS standard reference compound at a final concentration of 0.625 µM.

Some of the exemplified Examples disclosed below were tested in the Human GRP40 In Vitro assay described above and found having hGRP40 modulating activity reported as hGPR40 IP1 $EC_{50}$.

BMS DPP4i—Reference Compound

BMS DPP4i is disclosed in Simpkins, L. et al., *Bioorganic Medicinal Chemistry Letters*, 17(23):6476-6480 (2007) (compound 48) and in WO 2005/012249 (Example 3). BMS DPP4i has the following formula:

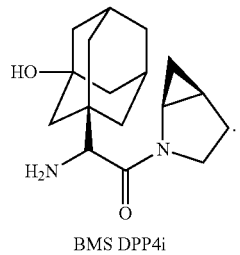

BMS DPP4i

The compounds of the present invention possess activity as modulators of GPR40, and, therefore, may be used in the treatment of diseases associated with GPR40 activity. Via modulation of GPR40, the compounds of the present invention may preferably be employed to modulate the production/secretion of insulin and/or gut hormones, such as GLP-1, GIP, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, vascular restenosis, peripheral arterial disease, lipid disorders, liver diseases such as NASH (Non-Alcoholic Steatohepatitis), NAFLD (Non-Alcoholic Fatty Liver Disease) and liver cirrhosis, neurodegenerative disease, cognitive impairment, dementia, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

GPR40 is expressed in neuronal cells, and is associated with development and maintenance of neuronal health in brain, as described in Yamashima, T., *Progress in Neurobiology*, 84:105-115 (2008).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR40 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR40 receptor modulators, or other antidiabetic agents. These agents include, but are not limited to, dipeptidyl peptidase IV inhibitors (DPP4i; for example, sitagliptin, saxagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, tesaglitazar, aleglitazar), glucokinase activators (as described in Fyfe, M. C. T. et al., *Drugs of the Future*, 34(8):641-653 (2009) and incorporated herein by reference), other GPR40 receptor modulators (e.g., TAK-875), GPR119 receptor modulators (for example, MBX-2952, PSN821, APD597), GPR120 receptor modulators (for example, as described in Shimpukade, B. et al., *J. Med. Chem.*, 55(9): 4511-4515 (2012)), sodium-glucose transporter-2 (SGLT2) inhibitors (for example dapagliflozin, canagliflozin, empagliflozin, remagliflozin), 11b-HSD-1 inhibitors (for example MK-0736, BI35585, BMS-823778, and LY2523199), MGAT inhibitors (for example, as described in Barlind, J. G. et al., *Bioorg. Med. Chem. Lett.* (2013), doi: 10.1016/j.bmcl.2013.02.084), amylin analogs such as pramlintide, and/or insulin. Reviews of current and emerging therapies for the treatment of diabetes can be found in: Mohler, M. L. et al., *Medicinal Research Reviews*, 29(1):125-195 (2009), and Mizuno, C. S. et al., *Current Medicinal Chemistry*, 15:61-74 (2008).

The GPR40 receptor modulator of formula I may also be optionally employed in combination with agents for treating complication of diabetes. These agents include PKC inhibitors and/or AGE inhibitors.

The GPR40 receptor modulator of formula I way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with GPR40 (as defined previously). In another embodiment, the package insert states that the pharmaceutical composition can be used in combination (as defined previously) with a second therapeutic agent for the treatment of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following method:

Linear Gradient of 0% to 100% Solvent B over 2 min, with 1 minute hold at 100% B;

UV visualization at 220 nm;

Column: PHENOMENEX® Luna C18 (2) 30 mm×4.60 mm; 5 m particle (Heated to Temp. 40° C.);

Flow rate: 5 ml/min;

Solvent A: 10% MeCN-90% $H_2O$-0.1% TFA; or, 10% MeOH-90% $H_2O$-0.1% TFA; and

Solvent B: 90% MeCN-10% $H_2O$-0.1% TFA; or, 90% MeOH-10% $H_2O$-0.1% TFA.

Preparatory HPLC (unless otherwise noted) was performed on a Shimadzu SCL-10A liquid chromatograph with a linear gradient of 20-100% Solvent B over 10 or 30 min, with either a 2 or 5 min (respectively) hold at 100% Solvent B;

UV visualization at 220 nm;

Column: PHENOMENEX® Luna Axia 5µ C18 30×100 mm;

Flow rate: 20 mL/min;

Solvent A: 10% MeCN-90% $H_2O$-0.1% TFA; and

Solvent B: 90% MeCN-10% $H_2O$-0.1% TFA.

Analytical HPLC (unless otherwise noted) was performed to determine compound purity on a Shimadzu SIL-10A using the following method (Unless otherwise stated, retention times listed in Examples refer the retention times of Column 1):

Linear Gradient of 10% to 100% Solvent B over 15 min;

UV visualization at 220 nm and 254 nm;

Column 1: SunFire C18 3.5 µm, 4.6×150 mm;

Column 2: XBridge Phenyl 3.5 µm, 4.6×150 mm;

Flow rate: 1 ml/min (for both columns);

Solvent A: 5% MeCN-95% $H_2O$-0.05% TFA; and

Solvent B: 95% MeCN-5% $H_2O$-0.05% TFA.

or

Linear Gradient of stated starting percentage to 100% Solvent B over 8 min;

UV visualization at 220 nm;

Column: ZORBAX® SB C18 3.5 µm, 4.6×75 mm;

Flow rate: 2.5 ml/min;

Solvent A: 10% MeOH-90% $H_2O$-0.2% $H_3PO_4$; and

Solvent B: 90% MeOH-10% $H_2O$-0.2% $H_3PO_4$.

NMR EMPLOYED IN CHARACTERIZATION OF EXAMPLES

¹H NMR spectra (unless otherwise noted) were obtained with JEOL® or Bruker FOURIER® transform spectrometers operating at 400 MHz or 500 MHz. ¹H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethylsilane=0 ppm) for ¹H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Example 1

2-((2S,3S,4R)-1-(5-((3R,4R)-1-(5-Chloro-2-methoxypyridin-4-yl)-3-methylpiperidin-4-yloxy)pyrazin-2-yl)-4-methoxy-3-methylpyrrolidin-2-yl)acetic acid

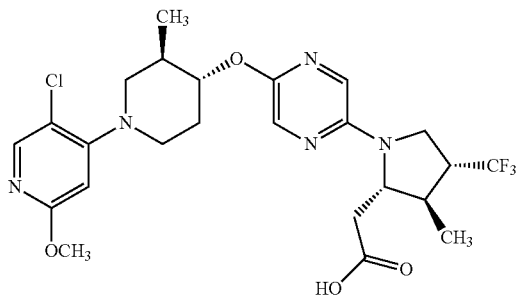 [SMILES: COc1cc(N2CC[C@@H](Oc3cnc(N4C[C@H](C(F)(F)F)[C@@H](C)[C@@H]4CC(=O)O)cn3)[C@H](C)C2)c(Cl)cn1]

1A. (2S,3S,4R)-Benzyl 2-(cyanomethyl)-4-methoxy-3-methylpyrrolidine-1-carboxylate: To a stirring solution of (2R,3S,4R)-benzyl 2-(hydroxymethyl)-4-methoxy-3-methylpyrrolidine-1-carboxylate (PCT/US2013/070213 filed Nov. 15, 2013) (780 mg, 2.79 mmol) in $CH_2Cl_2$ (10 mL) cooled at 0° C. was added $Et_3N$ (0.778 mL, 5.58 mmol), followed by dropwise addition of methanesulfonyl chloride (0.326 mL, 4.19 mmol). After addition, the resulting cloudy solution was stirred at 0° C. for 1 h. LC-MS showed the reaction was complete. The reaction mixture was diluted with EtOAc, washed with water (2×), sat. aq. $NaHCO_3$, brine (2×), dried ($Na_2SO_4$) and concentrated to dryness. The obtained oily residue was dried in high vacuum to afford the desired product (2R,3S,4R)-benzyl 4-methoxy-3-methyl-2-(((methylsulfonyl)oxy)methyl)pyrrolidine-1-carboxylate (1.0 g, 2.81 mmol, 100% yield), which was used immediately in the reaction described below.

The obtained mesylate was dissolved in anhydrous DMSO (10 mL). NaCN (547 mg, 11.16 mmol) was added in the solution. The resulting suspension was stirred at 50° C. for 16 h. LC-MS showed the reaction was complete. After cooling to rt, the reaction was quenched with water and extracted with EtOAc (3×). The combined extracts were washed with water, brine, dried ($Na_2SO_4$) and concentrated to dryness. The crude product was purified by flash chromatography eluting with EtOAc/hexanes (0-35%, 20 min; 35%, 5 min; 35-70%, 15 min). The desired fractions were pooled, concentrated and dried in high vacuum to afford (2S,3S,4R)-benzyl 2-(cyanomethyl)-4-methoxy-3-methylpyrrolidine-1-carboxylate (641 mg, 2.201 mmol, 79% yield) as a colorless oil. LC-MS Anal. Calc'd for $C_{16}H_{20}N_2O_3$: 288.15, found [M+H] 289.2. ¹H NMR (400 MHz, $CDCl_3$) δ 7.50-7.33 (m, 5H), 5.26-5.08 (m, 2H), 3.85-3.66 (m, 2H),), 3.61-3.47 (m, 2H), 3.36 (s, 3H), 3.06-2.69 (m, 2H), 2.49 (t, J=7.0 Hz, 1H), 1.21-0.98 (m, 3H).

1B. 2-((2S,3S,4R)-4-Methoxy-3-methylpyrrolidin-2-yl)acetonitrile: A suspension of 1A (80 mg, 0.277 mmol) and Pd/C (40 mg, 0.019 mmol) (5% dry basis, Degussa type) in EtOAc (5 mL) was vigorously stirred under a hydrogen balloon at rt for 14 h. LC-MS showed the reaction was complete. The reaction mixture was filtered and the catalyst washed with EtOAc. The combined filtrate was concentrated to dryness. The obtained residue was dried in high vacuum for 10 min to afford 2-((2S,3S,4R)-4-methoxy-3-methylpyrrolidin-2-yl)acetonitrile (41 mg, 0.253 mmol, 91% yield) as a colorless oil. LC-MS Anal. Calc'd for $C_8H_{14}N_2O$: 154.21, found [M+H] 155.1. ¹H NMR (400 MHz, $CDCl_3$) δ 3.40 (dt, J=5.1, 3.4 Hz, 1H), 3.30 (br, s, 1H), 3.24 (s, 3H), 3.06-2.94 (m, 2H), 2.89 (q, J=6.2 Hz, 1H), 2.56-2.40 (m, 2H), 1.82 (td, J=6.7, 3.6 Hz, 1H), 1.07-1.01 (m, 3H).

1C. (3R,4R)-1-Benzyl-3-methylpiperidin-4-ol: A 20 L reactor was sequentially rinsed with 2.0 L of methanol and 2.0 L of MILLI-Q® water. The reactor was charged with 1.0 Kg of 1-benzyl-3-methylpiperidin-4-one and 7.8 L of water under nitrogen atmosphere at 25° C. The vessel was charged with 1.2 Kg of D-(+)-glucose, 1.0 L of pH 7.0 phosphate buffer and 0.5 L of pH 7.4 tris-chloride buffer, and the mixture was stirred for 10 min. To the solution was added nicotinamide adenine dinucleotide (6.64 g) and 20 g of glucose dehydrogenase (GDH-105, Codexis). The reaction temperature was gradually raised to 30° C. and the solution was agitated for 36 hrs. The reaction mixture was cooled to 10° C. and the pH was adjusted to 11 with NaOH. The resulting solution was stirred for 1 hr and it was filtered through a 10 µm filter cloth. The solids were washed with water and allowed to suction dry for 3 hrs. The residue was dissolved in 20 L of MTBE and insoluble material was removed via filtration. The organic layer was concentrated to 3.0 Kg weight and 5.0 L of heptane was added. The solution was concentrated at 45° C. to 5 Kg weight followed by stirring for 1 h during crystallization. The mixture was filtered and the solids were dried to give 0.785 Kg of 1C as a pale yellow solid. ¹H NMR (400 MHz, $CDCl_3$) δ 7.33-7.24 (m, 5H), 3.48 (s, 2H), 3.14-3.13 (m, 1H), 2.88-2.77 (m, 2H), 2.05 (dd, J=2.8, 12 Hz, 1H), 1.99-1.87 (m, 1H), 1.73-1.58 (m, 4H), 0.95 (d, J=6.4, 3H).

1D. (3R,4R)-3-Methylpiperidin-4-ol: Methanol (7.85 L) and 1C (0.785 Kg) were charged into a 10 L autoclave, and the solution was stirred for 15 min. To this solution was added 78.5 g of 10% palladium hydroxide) and 43 mL of acetic acid. The atmosphere was purged with nitrogen for 15 min, and hydrogen gas pressure (4 kg) was applied to the autoclave. The reaction mixture was stirred under hydrogen for 15 hrs and the solution was filtered through a bed of CELITE® that was subsequently washed with methanol. The filtrates were combined and evaporated to give 0.545 Kg of 1D as a colorless semi-solid. ¹H NMR (400 MHz, DMSO-$d_6$) δ 4.80 (br s, 2H), 3.00-2.82 (m, 3H), 2.51-2.44 (m, 1H), 2.12 (t, J=11.2 Hz, 1H), 1.76-1.70 (m, 2H), 1.35-1.30 (m, 2H), 0.97 (d, J=6.5 Hz, 3H).

1E. 4-Bromo-2-methoxypyridine: A heterogeneous reaction mixture of 4-bromo-2-fluoropyridine (2.64 mL, 25.6 mmol) and NaOMe (8.29 g, 153 mmol) in MeOH (36.5 mL) was reacted in a pressure tube at 155° C. for 5 h. The reaction mixture was cooled to rt and the solids were filtered and washed with EtOAc. The filtrate was concentrated to a pale yellow oil with some white solids. The oil yellow was decanted and diluted with water and the solution was extracted with EtOAc (2×). The combined organic layers were washed with water and brine, dried over $MgSO_4$, filtered, and concentrated to obtain 1E (4.43 g, 21.20 mmol, 83% yield) as a yellow oil. LC-MS Anal. Calc'd for $C_6H_6BrNO$: 188.02, found [M+H] 187.9, 189.9. $^1H$ NMR (400 MHz, $CDCl_3$) δ 7.98 (d, J=5.5 Hz, 1H), 7.02 (dd, J=5.5, 1.5 Hz, 1H), 6.94 (d, J=1.8 Hz, 1H), 3.92 (s, 3H).

1F. 4-Bromo-5-chloro-2-methoxypyridine: To a solution of 1E (2.00 g, 10.6 mmol) in DMF (21 mL) was added NCS (2.98 g, 22.3 mmol). The reaction mixture was stirred at rt overnight. The reaction mixture was quenched with water, diluted with EtOAc, and the layers were separated. The aqueous layer was extracted with EtOAc and the combined organic extracts were washed with brine, dried over $MgSO_4$, and concentrated. The crude product was purified by silica chromatography to provide 1F (2.15 g, 9.18 mmol, 86% yield) as a white solid. LC-MS Anal. Calc'd for $C_6H_5BrClNO$: 220.92, found [M+H] 223.8. $^1H$ NMR (400 MHz, $CDCl_3$) δ 8.15 (s, 1H), 7.05 (s, 1H), 3.91 (s, 3H).

1G. (3,4-trans)-1-(5-Chloro-2-methoxypyridin-4-yl)-3-methylpiperidin-4-ol: To a solution of 1D (0.28 Kg) and 1F (0.44 Kg) in DMSO (3.4 L) was added $K_2CO_3$ (0.95 Kg) and the mixture was heated to 115-120° C. for 16 hrs. The reaction mixture was cooled to rt and water (6.8 L) and ethyl acetate (2.25 L) were added with stirring for 15 min. The layers were separated and the aqueous layer was re-extracted with 2.25 L of ethyl acetate. The combined organic layers were washed with 1.5 N aq. HCl (1.8 L). The aqueous layer was re-extracted with ethyl acetate, and the combined aqueous layers were pH adjusted to 8 with 10% sodium bicarbonate and the mixture was extracted with ethyl acetate (2.25 L). The layers were separated and the aqueous layer was re-extracted with ethyl acetate. The combine organic layers were successively extracted with brine, dried over sodium sulfate, filtered, and evaporated to give 0.4 Kg of 1G as a dark brown semi-solid. $^1H$ NMR (400 MHz, DMSO-$d_6$) δ 7.99 (s, 1H), 6.35 (s, 1H), 4.70 (d, J=5.2 Hz, 1H), 3.80 (s, 3H), 3.47-3.37 (m, 2H), 2.77-2.71 (m, 1H), 2.49-2.39 (m, 1H), 1.90-1.86 (m, 1H), 1.59-1.56 (m, 2H), 1.49 (d, J=5.5 Hz, 1H), 0.95 (d, J=7.0 Hz, 3H).

1H. 2-Chloro-5-((3R,4R)-1-(5-chloro-2-methoxypyridin-4-yl)-3-methylpiperidin-4-yloxy)pyrazine: To a solution of (3R,4R)-1-(5-chloro-2-methoxypyridin-4-yl)-3-methylpiperidin-4-ol (630 mg, 2.454 mmol) in DMF (7 mL) cooled at 0° C. was added NaH (60% in mineral oil) (147 mg, 3.68 mmol) in one portion. The resulting suspension was stirred at rt for 20 min, then cooled at 0° C. 2,5-dichloropyrazine (804 mg, 5.40 mmol) was added in and the resulting brownish mixture was stirred at rt for 4 h. LC-MS showed the desired product formed as a major product. The reaction mixture was cooled at 0° C. and quenched by dropwise addition of water. The mixture was partitioned between EtOAc and water. The separated aqueous phase was extracted with EtOAc (2×). The combined EtOAc extracts were washed with water (2×), brine, dried ($Na_2SO_4$) and concentrated to give a light brown oil. The crude product was purified by flash chromatography eluting with EtOAc/hexanes (0-10%, 15 min; 10-20%, 10 min; 20%, 10 min). The desired fractions were pooled, concentrated and dried in high vacuum to afford 1H (825 mg, 2.234 mmol, 91% yield) as a white solid. LC-MS Anal. Calc'd for $C_{16}H_{18}Cl_2N_4O_2$: 368.081, found [M+H] 369.1 and 371.1. $^1H$ NMR (400 MHz, $CDCl_3$) δ 8.10-7.97 (m, 3H), 6.28 (s, 1H), 4.82 (td, J=9.2, 4.4 Hz, 1H), 3.92 (s, 3H), 3.62-3.52 (m, 2H), 3.01-2.87 (m, 1H), 2.67 (dd, J=12.3, 9.7 Hz, 1H), 2.35-2.11 (m, 2H), 1.91-1.75 (m, 1H), 1.09-0.98 (d, J=6.6 Hz, 3H).

1I. 2-((2S,3S,4R)-1-(5-((3R,4R)-1-(5-Chloro-2-methoxypyridin-4-yl)-3-methylpiperidin-4-yloxy)pyrazin-2-yl)-4-methoxy-3-methylpyrrolidin-2-yl)acetonitrile: To a microwave vial containing 1H (36.5 mg, 0.099 mmol) was added a solution of 1B (18.29 mg, 0.119 mmol) in dioxane (0.6 mL), followed by palladium(II) acetate (2.219 mg, 9.89 μmol, sodium tert-butoxide (23.75 mg, 0.247 mmol) and 1,1'-bis(di-tert-butylphosphino)ferrocene (94 mg, 0.198 mmol). The vial was sealed and heated at 100° C. for 1 h under microwave irradiation. LC-MS showed formation of the desired product. After cooling to rt, the reaction mixture was diluted with water and extracted with DCM (3×). The combined extracts were washed with brine, dried ($MgSO_4$) and concentrated to give a dark oily residue, which was purified by flash chromatography eluting with EtOAc/hexanes (0-30%, 20 min; 30%, 10 min; 30-50%, 10 min). The desired fractions were pooled, concentrated and dried in high vacuum to give the desired product 1I (40 mg, 0.078 mmol, 79% yield) as a brownish oil. LC-MS Anal. Calc'd for $C_{24}H_{31}ClN_6O_3$: 486.215, found [M+H] 487.3. $^1H$ NMR (400 MHz, $CDCl_3$) δ 8.00 (s, 1H), 7.85 (s, 1H), 7.40 (s, 1H), 6.30 (s, 1H), 4.66 (td, J=9.0, 4.0 Hz, 1H), 4.07-3.97 (m, 1H), 3.92 (s, 3H), 3.76-3.46 (m, 4H), 3.43 (s, 3H), 3.10-2.75 (m, 3H), 2.71-2.55 (m, 2H), 2.34-2.12 (m, 2H), 1.93-1.63 (m, 2H), 1.15-0.98 (m, 6H).

Example 1: To a microwave vial containing 1I (39 mg, 0.080 mmol) was added ethanol (0.5 mL) and 6 M aqueous solution of KOH (0.28 mL). The reaction vial was sealed and stirred at 120° C. for 4.5 h, LC-MS showed the reaction was complete. After cooling to rt, the reaction was concentrated to remove most of the EtOH. The remaining aqueous was adjusted to pH 6 with 1 N aq. HCl. The resulting suspension was diluted with water and extracted with DCM (3×). The combined extracts were washed with brine, dried ($MgSO_4$) and concentrated to dryness to give a crude product, which was purified by prep HPLC (0.1% TFA-MeOH—$H_2O$) (PHENOMENEX® Luna Axia 5μ 30×100, gradient 60-90% over 10 min, hold at 90% for 5 min). The desired fractions were pooled and concentrated to remove the volatiles. The remaining aqueous was adjusted to pH 6 with sat. aq. $NaHCO_3$, then extracted with DCM (3×). The combined extracts were washed with brine, dried ($MgSO_4$) and concentrated to give a glassy residue, which was lyophilized in $CH_3CN$/water to afford the desired product Example 1 (16.8 mg, 0.032 mmol, 40.0% yield) as a white lyophilate. LC-MS Anal. Calc'd for $C_{24}H_{32}ClN_5O_5$: 505.21, found [M+H] 506.5. $^1H$ NMR (400 MHz, $CDCl_3$) δ 8.01 (d, J=0.9 Hz, 1H), 7.83 (d, J=1.3 Hz, 1H), 7.48 (br. s., 1H), 6.30 (s, 1H), 4.71-4.58 (m, 1H), 4.08-3.98 (m, 1H), 3.93 (s, 3H), 3.72 (br. s., 1H), 3.64-3.52 (m, 4H), 3.41 (s, 3H), 3.05-2.89 (m, 2H), 2.87-2.77 (m, 1H), 2.73-2.62 (m, 1H), 2.56-2.43 (m, 1H), 2.32-2.15 (m, 3H), 1.83 (m, 1H), 1.08 (m, 6H). hGPR40 $EC_{50}$=72 nM. hGPR40 IP1 $EC_{50}$=14 nM.

Example 2

2-((2S,3S,4R)-1-(5-((3R,4R)-1-(5-Chloro-2-methoxypyridin-4-yl)-3-methylpiperidin-4-yloxy)pyrazin-2-yl)-4-(3-methoxypropoxy)-3-methylpyrrolidin-2-yl)acetic acid

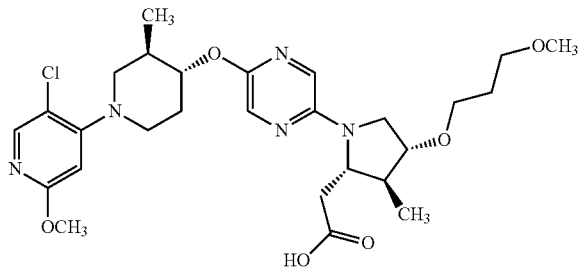 [SMILES: COCCCO[C@H]1CN(c2cnc(O[C@@H]3CCN(c4cc(OC)ncc4Cl)C[C@H]3C)cn2)[C@@H](CC(=O)O)[C@@H]1C]

2A. (R)-1-Benzyl 2-methyl 4-((tert-butyldimethylsilyl)oxy)-4,5-dihydro-1H-pyrrole-1,2-dicarboxylate: To a solution of (2S,4R)-methyl 4-hydroxypyrrolidine-2-carboxylate, HCl (10.0 g, 55.3 mmol) in CH$_2$Cl$_2$ (76 mL) at rt was added imidazole (8.66 g, 127 mmol) and TBS-Cl (9.17 g, 60.8 mmol). The reaction mixture was stirred at rt overnight. The reaction mixture was washed with 10% aq. Na$_2$CO$_3$ (75 mL). The layers were separated and the aqueous layer was extracted with CH$_2$Cl$_2$ (75 mL). The combined organic layers were concentrated to a small volume and then toluene was added and the fractions were concentrated to ~75 mL. The toluene phase was washed with water and then used directly in the next step. To the solution of (2S,4R)-methyl 4-((tert-butyldimethylsilyl)oxy)pyrrolidine-2-carboxylate in toluene cooled to 0° C. was added water (25 mL) followed by NaDCC (6.69 g, 30.4 mmol). After 30 min, the reaction mixture was filtered through CELITE®, washed with toluene (30 mL), and the phases were separated. The organic phase was washed with water, cooled to 0° C., and NEt$_3$ (9.3 mL, 66 mmol) was added. The reaction mixture was stirred for 1 h at 0° C. and then overnight at rt. The organic solution was washed with water (2×), dried (MgSO$_4$), and concentrated. The crude material was used directly in the next step without further purification. To a solution of (R)-methyl 3-((tert-butyldimethylsilyl)oxy)-3,4-dihydro-2H-pyrrole-5-carboxylate in CH$_2$Cl$_2$ (101 mL) at −10° C. was added 2,6-lutidine (11.8 mL, 101 mmol) followed by the dropwise addition of benzyl chloroformate (7.9 mL, 56 mmol) and the reaction mixture was warmed to rt and stirred overnight. Ethylenediamine (0.50 mL, 7.4 mmol) was added to the reaction mixture, which was stirred for 15 min at rt and then washed with 1 N aq. citric acid (60 mL) and 1 N aq. HCl (50 mL). The organic layer was washed with water, 1.5 N aq. KH$_2$PO$_4$, and brine. The organic layer was dried (Na$_2$SO$_4$), filtered, and concentrated. The crude product was purified by silica chromatography to provide 2A (16.3 g, 41.6 mmol, 82% yield) as a colorless oil. LC-MS Anal. Calc'd for C$_{20}$H$_{29}$NO$_5$Si: 391.55, found [M+H] 392.0. $^1$H NMR (500 MHz, CDCl$_3$) δ 7.40-7.29 (m, 5H), 5.69-5.62 (m, 1H), 5.20-5.11 (m, 2H), 4.94 (dt, J=7.7, 3.2 Hz, 1H), 3.98 (dd, J=12.4, 8.0 Hz, 1H), 3.79 (dd, J=12.2, 3.4 Hz, 1H), 3.71-3.62 (m, 3H), 0.88 (s, 9H), 0.07 (d, J=3.3 Hz, 6H).

2B. (2R,3S,4R)-1-Benzyl 2-methyl 4-((tert-butyldimethylsilyl)oxy)-3-methylpyrrolidine-1,2-dicarboxylate: CuBr·SMe$_2$ (4.78 g, 23.2 mmol) was suspended in anhydrous Et$_2$O (51 mL) and cooled to −40° C. A 1.6 M solution of MeLi in Et$_2$O (29.1 mL, 46.5 mmol) was added dropwise via addition funnel. The solution was stirred for 1 h and then a solution of 2A (7.00 g, 17.9 mmol) in Et$_2$O (20.4 mL) was added dropwise via addition funnel. The reaction mixture was stirred for 45 min at −45° C. and then transferred via cannula to a vigorously stirred solution of sat. aq. NH$_4$Cl and stirred for 30 min. The organic layer was separated and washed with sat. aq. NH$_4$Cl. The combined aqueous layers were extracted with hexanes. The combined organic layers were dried (MgSO$_4$) and concentrated. The crude material was purified by silica chromatography to obtain 2B (5.11 g, 12.5 mmol, 70% yield) as a colorless oil. LC-MS Anal. Calc'd for C$_{21}$H$_{33}$NO$_5$Si: 407.58, found [M+H] 408.2. $^1$H NMR (500 MHz, CDCl$_3$) δ (two rotamers) 7.40-7.27 (m, 5H), 5.21-5.00 (m, 2H), 4.01-3.90 (m, 1H), 3.87-3.80 (m, 1.6H), 3.77-3.71 (s and m, 1.8H), 3.57 (s, 1.6H), 3.36-3.28 (m, 1H), 2.33-2.25 (m, 1H), 1.11 (dd, J=7.2, 2.2 Hz, 3H), 0.86 (s, 9H), 0.08-0.01 (m, 6H).

2C. (2R,3S,4R)-1-Benzyl 2-methyl 4-hydroxy-3-methylpyrrolidine-1,2-dicarboxylate: To a solution of 2B (5.10 g, 12.5 mmol) in THF (42 mL) was added a 1 M solution of TBAF in THF (19 mL, 19 mmol) and the reaction mixture was stirred at rt for 1 h. The reaction mixture was diluted with EtOAc and washed with water and brine, dried (MgSO$_4$), and concentrated. The crude material was purified by silica chromatography to obtain 2C (3.61 g, 12.3 mmol, 98% yield) as a colorless oil, which crystallized to a white solid upon standing. LC-MS Anal. Calc'd for C$_{15}$H$_{19}$NO$_5$: 293.32, found [M+H] 294.0. $^1$H NMR (400 MHz, CDCl$_3$) δ 7.41-7.27 (m, 5H), 5.25-4.97 (m, 2H), 4.09-3.96 (m, 1H), 3.95-3.87 (m, 1H), 3.86-3.70 (m, 3H), 3.69-3.57 (m, 2H), 3.10-2.83 (m, 1H), 2.37 (td, J=6.9, 2.9 Hz, 1H), 1.12 (d, J=7.3 Hz, 3H).

2D. (2R,3S,4R)-1-Benzyl 2-methyl 4-(allyloxy)-3-methylpyrrolidine-1,2-dicarboxylate: To a solution of 2C (0.405 g, 1.38 mmol) in DMF (6.9 mL) at 0° C. was added 60% NaH (0.083 g, 2.1 mmol). The reaction mixture was stirred for 30 min and then allyl bromide (0.18 mL, 2.1 mmol) was added. The reaction mixture was warmed to rt and stirred for 1 h. The reaction mixture was quenched with water and diluted with EtOAc. The layers were separated and the organic layer was washed with water (4×). The organic layer was washed with brine, dried (MgSO$_4$), and concentrated. The crude product was purified by silica chromatography to provide 2D (0.446 g, 1.34 mmol, 97% yield) as a colorless oil. LC-MS Anal. Calc'd for C$_{18}$H$_{23}$NO$_5$: 333.38, found [M+H] 334.0. $^1$H NMR (500 MHz, CDCl$_3$) δ (two rotamers) 7.41-7.27 (m, 5H), 5.90-5.77 (m, 1H), 5.29-4.99 (m, 4H), 4.09-3.90 (m, 3H), 3.86 and 3.80 (2 dd, J=11.3, 5.6 Hz, 1H), 3.73 and 3.57 (2 s, 3H), 3.67-3.61 (m, 1H), 3.46 (ddd, J=11.0, 6.1, 4.7 Hz, 1H), 2.59-2.44 (m, 1H), 1.14 (dd, J=7.2, 1.1 Hz, 3H).

2E. (2R,3S,4R)-1-Benzyl 2-methyl 4-(3-hydroxypropoxy)-3-methylpyrrolidine-1,2-dicarboxylate: To a solution of 2D (2.74 g, 8.20 mmol) in THF (4.1 mL) at 0° C. was added a 1 M solution of BH$_3$·THF (2.8 mL, 2.8 mmol) in THF. After 15 min, the reaction mixture was stirred at rt for 2.2 h. Additional BH$_3$·THF (1 M in THF) (0.2 mL, 0.2 mmol) was added and the reaction mixture was stirred for an additional 15 min. Water (4.1 mL) and sodium perborate·4H$_2$O (1.29 g, 8.37 mmol) were added. After stirring for 2 h, the reaction mixture was diluted with EtOAc, washed with brine, dried (MgSO$_4$), and concentrated. The crude product was purified by silica chromatography to provide 2E (2.17 g, 6.18 mmol, 75% yield) as a colorless oil. LC-MS Anal. Calc'd for C$_{18}$H$_{25}$NO$_6$: 351.39, found [M+H] 352.0. $^1$H NMR (500 MHz, CDCl$_3$) δ (two rotamers)

7.43-7.27 (m, 5H), 5.26-5.00 (m, 2H), 4.18-3.98 (m, 1H), 3.84-3.76 (m, 1H), 3.75 and 3.61 (two s, 3H), 3.73-3.66 (m, 2H), 3.61-3.50 (m, 4H), 2.62-2.50 (m, 1H), 2.04-2.00 (m, 1H), 1.77 (quind, J=5.7, 2.9 Hz, 2H), 1.12 (d, J=7.2 Hz, 3H).

2F. (2R,3S,4R)-1-Benzyl 2-methyl 4-(3-methoxypropoxy)-3-methylpyrrolidine-1,2-dicarboxylate: To a solution of 2E (2.17 g, 6.18 mmol) in MeCN (7.7 mL) was added $Ag_2O$ (3.58 g, 15.4 mmol) and MeI (3.9 mL, 62 mmol). The reaction mixture was stirred at 50° C. for 18 h. The mixture was filtered and concentrated. The crude product was purified by silica chromatography to provide 2F (2.71 g, 7.42 mmol, 81% yield). LC-MS Anal. Calc'd for $C_{19}H_{27}NO_6$: 365.42, found [M+H] 367.0. $^1$H NMR (500 MHz, $CDCl_3$) δ 7.41-7.27 (m, 5H), 5.24-4.99 (m, 2H), 4.08-3.94 (m, 1H), 3.89-3.76 (m, 1H), 3.73, 3.58 (2 s, 3H), 3.57-3.53 (m, 1H), 3.51-3.42 (m, 3H), 3.40 (t, J=6.2 Hz, 2H), 3.32, 3.3 (2 s, 3H), 2.49 (dtd, J=6.9, 4.7, 2.2 Hz, 1H), 1.76 (quind, J=6.3, 2.1 Hz, 2H), 1.13 (dd, J=7.2, 3.0 Hz, 3H).

2G. (2R,3S,4R)-Benzyl 2-(hydroxymethyl)-4-(3-methoxypropoxy)-3-methylpyrrolidine-1-carboxylate: To a solution of 2F (4.13 g, 11.3 mmol) in THF (57 mL) at 0° C. was added a 2 M solution of $LiBH_4$ (11.3 mL, 22.6 mmol) in THF. The reaction mixture was warmed to rt and stirred for 17 h. The reaction mixture was cooled to 0° C., carefully quenched with sat. aq. $NH_4Cl$, and diluted with EtOAc/water. The layers were separated and the organic layer was washed with brine, dried ($MgSO_4$), and concentrated. The crude product was purified by silica chromatography to provide 2G (3.25 g, 9.15 mmol, 81%) as a colorless oil. LC-MS Anal. Calc'd for $C_{18}H_{27}NO_5$: 337.41, found [M+H] 338.0. $^1$H NMR (500 MHz, $CDCl_3$) δ 7.40-7.28 (m, 5H), 5.14 (s, 2H), 4.41-4.31 (m, 1H), 3.85-3.70 (m, 3H), 3.69-3.61 (m, 1H), 3.57-3.47 (m, 3H), 3.46-3.39 (m, 2H), 3.34-3.26 (m, 3H), 2.06-1.94 (m, 1H), 1.81 (quin, J=6.4 Hz, 2H), 1.09 (dd, J=9.9, 7.2 Hz, 3H).

2H. ((2R,3S,4R)-4-(3-Methoxypropoxy)-3-methylpyrrolidin-2-yl)methanol: A mixture of 2G (3.25 g, 9.63 mmol) and Pd/C (0.820 g, 0.771 mmol) in MeOH (193 mL) was purged with argon (3×) and then $H_2$ (3×). The reaction mixture was stirred under $H_2$ (1 atm) at rt for 3.5 h. The mixture was filtered through CELITE® and concentrated to give 2H (2.03 g, 9.99 mmol, 100% yield). LC-MS Anal. Calc'd for $C_{10}H_{21}NO_3$: 203.28, found [M+H] 204.1. $^1$H NMR (500 MHz, $CDCl_3$) δ 3.63 (dd, J=11.1, 3.4 Hz, 1H), 3.55-3.49 (m, 2H), 3.47 (t, J=6.3 Hz, 2H), 3.43 (td, J=6.3, 2.1 Hz, 2H), 3.31 (s, 3H), 3.06-3.00 (m, 1H), 2.98-2.90 (m, 1H), 2.85-2.76 (m, 1H), 1.85 (dt, J=6.9, 3.4 Hz, 1H), 1.83-1.75 (m, 2H), 1.05 (d, J=7.2 Hz, 3H).

2I. (2R,3S,4R)-Benzyl 2-(hydroxymethyl)-4-(3-methoxypropoxy)-3-methylpyrrolidine-1-carboxylate: To a stirring suspension of 2H (0.950 g, 4.67 mmol) and sodium bicarbonate (0.491 g, 5.84 mmol) in a mixed solvent of DCM (10 mL) and water (10 mL) at rt was added benzyl carbonochloridate (0.843 mL, 5.61 mmol) dropwise over 5 min. After addition, the mixture was vigorously stirred at rt for 1 h, LC-MS showed the reaction was not complete. About 0.2 mL of benzyl chloroformate was added. After stirring for one more hour, the reaction was quenched with water. The mixture was extracted with EtOAc (3×). The combined extracts were washed with water, brine, dried ($MgSO_4$) and concentrated. The crude product was purified by flash chromatography eluting with hexane/EtOAc (0%-50%, 20 min; 50%, 10 min; 50-100%, 15 min; 100%, 10 min). The desired fractions were pooled, concentrated and dried in vacuum to afford 2I (0.954 g, 2.80 mmol, 60% yield) as a colorless oil, LC-MS Anal. Calc'd for $C_{18}H_{27}NO_5$: 337.19, found [M+H] 338.1. $^1$H NMR (400 MHz, $CDCl_3$) δ 7.43-7.32 (m, 5H), 5.20-5.14 (m, 2H), 4.43 (dd, J=7.9, 3.1 Hz, 1H), 3.86-3.76 (m, 2H), 3.71-3.64 (m, 1H), 3.59-3.50 (m, 3H), 3.48-3.42 (m, 2H), 3.34 (s, 2H), 2.06-1.96 (m, 1H), 1.83 (quin, J=6.1 Hz, 2H), 1.14-1.07 (m, 3H), 1.16-1.07 (m, 3H).

2J. (2S,3S,4R)-Benzyl 2-(cyanomethyl)-4-(3-methoxypropoxy)-3-methylpyrrolidine-1-carboxylate: To a stirring solution of 2I (0.954 g, 2.83 mmol) in DCM (12 mL) cooled at 0° C. was added $Et_3N$ (0.788 mL, 5.65 mmol), followed by dropwise addition of methanesulfonyl chloride (0.330 mL, 4.24 mmol) over 5 min. After addition, the resulting cloudy solution was stirred at 0° C. for 1 h. LC-MS showed the reaction was complete. The reaction mixture was diluted with EtOAc, washed with water (2×), sat. aq. $NaHCO_3$, brine, dried ($MgSO_4$) and concentrated to dryness. The obtained residue was dried in high vacuum to afford (2R,3S,4R)-benzyl 4-(3-methoxypropoxy)-3-methyl-2-(((methylsulfonyl)oxy)methyl)pyrrolidine-1-carboxylate as an oily residue, which was used immediately for the reaction describe below.

The obtained mesylate was dissolved in anhydrous DMSO (9 mL). NaCN (555 mg, 11.32 mmol) was added in the solution. The resulting suspension was stirred at 50° C. for 16 h. LC-MS showed the reaction was complete. After cooling to rt, the reaction was quenched with water, and extracted with EtOAc (3×). The combined extracts were washed with water (2×), brine, dried ($MgSO_4$) and concentrated to dryness. The crude product was purified by flash chromatography eluting with EtOAc/hexanes (0-60%, 15 min; 60%, 10 min; 60-100%, 10 min) to afford 2J (830 mg, 2.372 mmol, 84% yield) as a colorless oil. LC-MS Anal. Calc'd for $C_{19}H_{26}N_2O_4$: 346.189, found [M+H] 347.1. $^1$H NMR (400 MHz, $CDCl_3$) δ 7.49-7.32 (m, 5H), 5.30-5.06 (m, 2H), 3.85-3.41 (m, 8H), 3.35 (s, 3H), 3.04-2.71 (m, 2H), 2.53-2.34 (m, 1H), 1.84 (quin, J=6.2 Hz, 2H), 1.19-0.96 (m, 3H).

2K. 2-((2S,3S,4R)-4-(3-Methoxypropoxy)-3-methylpyrrolidin-2-yl)acetonitrile: To a solution of 2J (430 mg, 1.24 mmol) in EtOAc (25 mL) was added Pd/C (210 mg, 0.099 mmol) (5% dry basis, Degussa type). After purging with hydrogen (3×), the suspension was vigorously stirred at rt under a hydrogen balloon for 16 h. LC-MS showed the reaction was complete. The mixture was filtered and the catalyst washed with EtOAc. The combined filtrate was concentrated to dryness. The obtained residue was dried in high vacuum for 30 min to afford 2K (251 mg, 1.12 mmol, 90% yield) as a pale yellow oil. LC-MS Anal. Calc'd for $C_{11}H_{20}N_2O_2$: 212.152, found [M+H] 213.4. $^1$H NMR (400 MHz, $CDCl_3$) δ 3.48 (m, 1H), 3.43-3.34 (m, 4H), 3.29-3.22 (m, 4H), 3.09-3.01 (m, 1H), 2.99-2.85 (m, 2H), 2.58-2.37 (m, 2H), 1.88-1.69 (m, 3H), 1.05-1.01 (m, 3H).

2L. 2-((2S,3S,4R)-1-(5-(((3R,4R)-1-(5-Chloro-2-methoxypyridin-4-yl)-3-methylpiperidin-4-yl)oxy)pyrazin-2-yl)-4-(3-methoxypropoxy)-3-methylpyrrolidin-2-yl)acetonitrile: To a microwave vial containing 1C (55.4 mg, 0.15 mmol) was added a solution of 2K (35.0 mg, 0.165 mmol) in dioxane (0.8 mL), followed by 1,1'-bis(di-tert-butylphosphino)ferrocene (142 mg, 0.300 mmol), palladium(II) acetate (3.37 mg, 0.015 mmol) and sodium tert-butoxide (36.0 mg, 0.375 mmol). The reaction mixture was bubbled with a stream of argon for 1 min, then the vial was sealed and heated at 100° C. for 1 h under microwave irradiation. LC-MS showed the desired product formed. After cooling to rt, the reaction mixture was diluted with water, extracted with DCM (3×). The combined DCM extracts were washed with brine, dried ($MgSO_4$) and concentrated to give a dark oily residue, which was purified by flash chromatography eluting with EtOAc/hexanes (0-30%, 20 min; 30%, 10 min;

30-50%, 10 min). The desired fractions were pooled, concentrated and dried in high vacuum to afford 2 L (81 mg, 0.13 mmol, 84% yield) as a brown oil. LC-MS Anal. Calc'd for $C_{27}H_{37}ClN_6O_4$: 544.256, found [M+H] 545.3. $^1$H NMR (400 MHz, CDCl$_3$) δ 8.00 (s, 1H), 7.84 (s, 1H), 7.39 (s, 1H), 6.30 (s, 1H), 4.66 (td, J=8.9, 4.0 Hz, 1H), 4.01 (d, J=8.1 Hz, 1H), 3.92 (s, 3H), 3.81 (br. s., 1H), 3.69-3.41 (m, 8H), 3.36 (s, 3H), 3.09-2.78 (m, 3H), 2.73-2.52 (m, 2H), 2.33-2.10 (m, 2H), 1.92-1.74 (m, 3H), 1.09 (m, 6H).

Example 2: To a microwave vial containing 2 L (80 mg, 0.125 mmol) was added EtOH (0.8 mL) and 6 M aqueous solution of KOH (0.49 mL). The reaction vial was sealed and stirred at 125° C. for 5 h, LC-MS showed the reaction was complete. After cooling to rt, the reaction mixture was concentrated to remove the volatile. The remaining aqueous was adjusted to pH 6 with 1N aq. HCl. The resulting white suspension was diluted with water, extracted with DCM (3×). The combined extracts were washed with brine, dried (MgSO$_4$) and concentrated to dryness. The obtained crude product was purified by prep HPLC (0.1% TFA-MeOH—H$_2$O) (PHENOMENEX® Luna Axia 5μ 30×100, gradient 60-100% over 12 min, hold at 100% for 3 min). The desired fractions were pooled and concentrated to remove the volatiles. The remaining aqueous suspension was adjusted to pH 6 with sat. aq. NaHCO$_3$, then extracted with DCM (3×). The DCM extracts were washed with brine, dried (MgSO$_4$) and concentrated to give a glassy residue, which was lyophilized in CH$_3$CN/water to afford Example 2 (15.8 mg, 0.027 mmol, 22% yield) as an off-white lyophilate. LC-MS Anal. Calc'd for $C_{27}H_{38}ClN_5O_6$: 563.251, found [M+H] 564.2. $^1$H NMR (400 MHz, CDCl$_3$) δ 8.01 (s, 1H), 7.83 (s, 1H), 7.47 (s, 1H), 6.30 (s, 1H), 4.65 (td, J=9.0, 4.1 Hz, 1H), 4.07-3.97 (m, 1H), 3.93 (s, 3H), 3.80 (d, J=2.2 Hz, 1H), 3.67-3.43 (m, 8H), 3.41-3.31 (m, 3H), 3.06-2.78 (m, 3H), 2.68 (t, J=10.9 Hz, 1H), 2.48 (d, J=7.3 Hz, 1H), 2.33-2.08 (m, 2H), 1.98-1.74 (m, 4H), 1.08 (m, 6H). hGPR40 EC$_{50}$=43 nM. hGPR40 IP1 EC$_{50}$=4 nM.

Example 3

2-((2S,3S,4R)-1-(5-(((3R,4R)-1-(5-Ethoxy-2-fluorophenyl)-3-methylpiperidin-4-yloxy)pyrazin-2-yl)-4-methoxy-3-methylpyrrolidin-2-yl)acetic acid

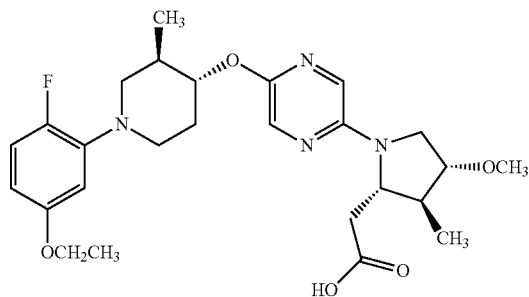 [SMILES: CCOc1ccc(F)c(N2CC[C@@H](Oc3cnc(N4C[C@H](OC)[C@@H](C)[C@@H]4CC(=O)O)cn3)[C@H](C)C2)c1]

3A. (3R,4R)-1-(5-Ethoxy-2-fluorophenyl)-3-methylpiperidin-4-yl benzoate: To a stirred solution of (3R,4S)-1-(5-ethoxy-2-fluorophenyl)-3-methylpiperidin-4-ol (300 mg, 1.18 mmol) (PCT/US2013/070213 filed Nov. 15, 2013), benzoic acid (174 mg, 1.42 mmol) and Ph$_3$P (373 mg, 1.42 mmol) in THF (6 mL) at rt was slowly added ADDP (0.28 mL, 1.4 mmol) dropwise over 5 min. After the addition, the resulting yellowish solution was stirred at rt for 1 h. The reaction mixture was concentrated to dryness. The residue was purified by silica chromatography to give 3A (198 mg, 0.554 mmol, 47% yield) as a white foam. LC-MS Anal. Calc'd for $C_{21}H_{24}FNO_3$: 357.42, found [M+H] 358.2.

3B. (3R,4R)-1-(5-Ethoxy-2-fluorophenyl)-3-methylpiperidin-4-ol: To a solution of 3A (200 mg, 0.560 mmol) in a solution of THF (2 mL), MeOH (0.5 mL), and water (1.5 mL) was added LiOH (134 mg, 5.60 mmol) in one portion. The resulting yellow solution was stirred at rt under argon for 16 h. The reaction was partially concentrated to remove the THF/MeOH and then cooled in an ice bath. 1 M aq. HCl was added to adjust the pH ~3-4. The product was extracted with CH$_2$Cl$_2$ (3×). The combined organic extracts were washed with brine, dried (MgSO$_4$), and concentrated. The resulting residue was purified by silica chromatography to give 3B (120 mg, 0.474 mmol, 85% yield) as a white foam. LC-MS Anal. Calc'd for $C_{14}H_{20}FNO_2$: 253.31, found [M+H] 254.1.

3C. 2-Chloro-5-(((3R,4R)-1-(5-ethoxy-2-fluorophenyl)-3-methylpiperidin-4-yl)oxy)pyrazine: To a stirring solution of 3B (440 mg, 1.737 mmol) in DMF (7 mL) cooled at 0° C. was added NaH (60% in mineral oil) (104 mg, 2.61 mmol). The resultant suspension was stirred at rt for 30 min and then cooled at 0° C. To this heterogeneous mixture was added 2,5-dichloropyrazine (518 mg, 3.47 mmol) (the reagent from Combi-Block was about 65% pure based on HPLC and LC-MS). The resulting brownish mixture was stirred at rt for 2 h. LCMS showed the reaction was not complete. The reaction was cooled at 0° C., 60 mg of NaH (60% in mineral oil) was added. After stirring at rt for 15 min, 150 mg of 2,5-dichloropyrazine was added. The reaction mixture was stirred at rt for additional 2.5 hours. After cooling to 0° C., the reaction mixture was quenched by dropwise addition of water. The resulting mixture was partitioned between EtOAc and water. The separated aqueous phase was extracted with EtOAc (3×). The combined extracts were washed with water (2×), brine, dried (Na$_2$SO$_4$) and concentrated to give a light brown solid. The crude product was purified by flash chromatography eluting with EtOAc/hexanes (0-10%, 20 min; 10%, 10 min; 10-20%, 10 min). The desired fractions were pooled, concentrated and dried in high vacuum to afford 3C (225 mg, 0.609 mmol, 35.1% yield) as a white solid. LC-MS Anal. Calc'd for $C_{18}H_{21}ClFN_3O_2$: 365.131, found [M+H] 366.0. $^1$H NMR (400 MHz, CDCl$_3$) δ 8.10 (d, J=1.3 Hz, 1H), 8.04 (d, J=1.3 Hz, 1H), 6.95 (dd, J=12.1, 8.8 Hz, 1H), 6.54 (dd, J=7.4, 3.0 Hz, 1H), 6.43 (dt, J=8.9, 3.2 Hz, 1H), 4.79 (td, J=9.6, 4.4 Hz, 1H), 4.01 (q, J=7.0 Hz, 2H), 3.54-3.37 (m, 2H), 2.97-2.81 (m, 1H), 2.60 (dd, J=12.1, 10.1 Hz, 1H), 2.35-2.12 (m, 2H), 1.88 (br. s., 1H), 1.43 (t, J=7.0 Hz, 3H), 1.05 (d, J=6.6 Hz, 3H).

3D. 2-((2S,3S,4R)-1-(5-(((3R,4R)-1-(5-Ethoxy-2-fluorophenyl)-3-methylpiperidin-4-yl)oxy)pyrazin-2-yl)-4-methoxy-3-methylpyrrolidin-2-yl)acetonitrile: To a microwave vial containing 3C (40 mg, 0.109 mmol) was added 1B (16.86 mg, 0.109 mmol) in dioxane (0.7 mL), followed by palladium(II) acetate (2.455 mg, 10.93 μmol), 1,1'-bis(di-tert-butylphosphino)ferrocene (104 mg, 0.219 mmol) and sodium tert-butoxide (26.3 mg, 0.273 mmol). The reaction vial was sealed and heated at 100° C. for 1 h under microwave irradiation. LC-MS showed the desired product formed. The reaction mixture was diluted with water, extracted with DCM (3×). The combined extracts were washed with brine, dried (MgSO$_4$) and concentrated to give a dark oily residue. The crude product was purified by flash chromatography eluting with EtOAc/hexanes (0-30%, 20 min; 30%, 10 min; 30-50%, 10 min) to afford 3D (21 mg, 0.043 mmol, 39.7% yield) as a white foam. LC-MS Anal. Calc'd for $C_{26}H_{34}FN_5O_3$: 483.26, found [M+H] 484.4. $^1$H NMR (400 MHz, CDCl$_3$) δ 7.85 (s, 1H), 7.40 (d, J=1.3 Hz, 1H), 6.94 (dd, J=12.2, 8.9 Hz, 1H), 6.55 (dd, J=7.4, 3.0 Hz, 1H), 6.42 (dt, J=8.8, 3.1 Hz, 1H), 4.61 (m, 1H), 4.06-3.93 (m, 3H), 3.73 (dt, J=4.0, 2.2 Hz, 1H), 3.63-3.53 (m, 2H), 3.47-3.43 (m, 2H), 3.43 (s, 3H), 3.05 (dd, J=16.4, 3.9 Hz, 1H), 2.95-2.77 (m, 2H), 2.69-2.54 (m, 1H), 2.30-2.08 (m, 2H), 1.91-1.58 (m, 2H), 1.44-1.39 (m, 3H), 1.16-1.02 (m, 6H).

Example 3: To a solution of 3D (20 mg, 0.041 mmol) in EtOH (0.4 mL) was added 6 M aqueous KOH solution (0.138 mL, 0.827 mmol). The reaction in a sealed vial was stirred at 125° C. for 2.5 h. LC-MS showed the desired product formed. After cooling to rt, the reaction was concentrated to remove the volatile. The remaining aqueous was adjusted to pH 5-6 with 1N aq. HC. The resulting suspension was extracted with DCM (3×). The combined DCM extracts were concentrated to dryness. The obtained residue was purified by prep HPLC (0.1% TFA-MeOH—H$_2$O) (PHENOMENEX® Luna Axia 5μ 30×100 (50-100% B for 12 min, 100% B hold for 3 min). The desired fractions were concentrated to remove the volatiles. The remaining aqueous phase was adjusted to pH 5-6 with sat. aq. NaHCO$_3$, then extracted with DCM (3×). The combined DCM extracts were washed with brine, dried (MgSO$_4$) and concentrated. The residue was lyophilized in CH$_3$CN/H$_2$O to give Example 3 (8.0 mg, 0.016 mmol, 38% yield) as an off-white powder. LC-MS Anal. Calc'd for $C_{26}H_{35}FN_4O_5$: 502.259, found [M+H] 503.2. $^1$H NMR (400 MHz, CD$_3$OD) δ 7.79 (d, J=1.5 Hz, 1H), 7.46 (d, J=1.3 Hz, 1H), 6.97-6.83 (m, 1H), 6.59-6.51 (m, 1H), 6.49-6.42 (m, 1H), 4.63-4.50 (m, 1H), 4.08-3.88 (m, 4H), 3.75-3.66 (m, 1H), 3.56 (s, 1H), 3.40-3.45 (m, 2H), 3.38 (s, 3H), 2.98-2.75 (m, 2H), 2.68-2.51 (m, 3H), 2.48-2.39 (m, 1H), 2.31-2.01 (m, 2H), 1.82-1.69 (m, 1H), 1.36 (t, J=6.9 Hz, 3H), 1.04 (dd, J=9.1, 7.2 Hz, 6H). hGPR40 EC$_{50}$=42 nM. hGPR40 IP1 EC$_{50}$=21 nM.

Example 4

2-((2S,3S,4R)-1-(5-(((3R,4R)-1-(5-Ethoxy-2-fluorophenyl)-3-methylpiperidin-4-yloxy)pyrazin-2-yl)-4-(3-methoxypropoxy)-3-methylpyrrolidin-2-yl)acetic acid

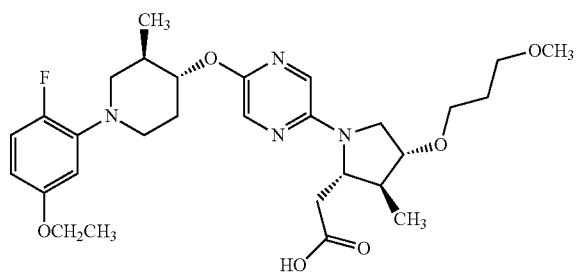 [SMILES: CCOc1ccc(F)c(N2CC[C@@H](Oc3cnc(N4C[C@H](OCCCOC)[C@@H](C)[C@@H]4CC(=O)O)cn3)[C@H](C)C2)c1]

4A. 2-((2S,3S,4R)-1-(5-(((3R,4R)-1-(5-Ethoxy-2-fluorophenyl)-3-methylpiperidin-4-yl)oxy)pyrazin-2-yl)-4-(3-methoxypropoxy)-3-methylpyrrolidin-2-yl)acetonitrile: To a microwave vial containing 2C (54.3 mg, 0.256 mmol) was added 3A (85 mg, 0.232 mmol), 1,1'-bis(di-tert-butylphosphino)ferrocene (220 mg, 0.465 mmol), palladium(II) acetate (5.22 mg, 0.023 mmol) and sodium tert-butoxide (55.8 mg, 0.581 mmol), followed by dioxane (1.3 mL). The reaction mixture was bubbled by a stream of argon for 1 min, then the vial was sealed and heated at 100° C. for 1 h under microwave irradiation. LC-MS showed the desired product formed. After cooling to rt, the reaction mixture was diluted with water, extracted with DCM (3×). The combined extracts were washed with brine, dried (MgSO$_4$) and concentrated to give a dark oily residue. The crude product was purified by flash chromatography eluting with EtOAc/hexanes (0-30%, 20 min; 30%, 10 min; 30-50%, 10 min). The desired fractions were pooled, concentrated and dried in high vacuum to afford 2-((2S,3S,4R)-1-(5-(((3R,4R)-1-(5-ethoxy-2-fluorophenyl)-3-methylpiperidin-4-yl)oxy) pyrazin-2-yl)-4-(3-methoxypropoxy)-3-methylpyrrolidin-2-yl)acetonitrile (58.5 mg, 0.092 mmol, 39.5% yield) as a brownish oil. LC-MS Anal. Calc'd for $C_{29}H_{40}FN_5O_4$: 541.306, found [M+H] 542.2. $^1$H NMR (400 MHz, CDCl$_3$) δ 7.78-7.73 (s, 1H), 7.30 (d, J=1.3 Hz, 1H), 6.84 (dd, J=12.1, 8.8 Hz, 1H), 6.45 (dd, J=7.5, 2.9 Hz, 1H), 6.32 (dt, J=8.8, 3.1 Hz, 1H), 4.51 (td, J=9.5, 4.2 Hz, 1H), 3.97-3.80 (m, 3H), 3.75-3.65 (m, 1H), 3.58-3.32 (m, 6H), 3.27 (s, 3H), 3.00-2.87 (m, 1H), 2.84-2.68 (m, 2H), 2.54-2.40 (m, 2H), 2.22-2.01 (m, 2H), 1.86-1.63 (m, 3H), 1.41-1.28 (m, 3H), 1.25-1.14 (m, 2H), 1.08-0.84 (m, 6H).

Example 4: To a microwave vial containing 4A (58 mg, 0.107 mmol) was added EtOH (0.6 mL) and 6 M aqueous solution of KOH (0.357 mL, 2.142 mmol). The reaction was sealed and stirred at 120° C. for 3 h. LC-MS showed the desired product formed. After cooling to rt, the reaction mixture was concentrated to remove the volatiles. The remaining aqueous phase was adjusted to pH 5-6 with 1 N aq. HCl. The resulting suspension was diluted with water and extracted with DCM (3×). The combined extracts were washed with brine, dried (MgSO$_4$) and concentrated to dryness. The crude product was purified by prep HPLC (0.1% TFA-MeOH—H$_2$O) (PHENOMENEX® Luna Axia 5μ 30×100, gradient 70-100% over 12 min, hold at 100% for 3 min). The desired fractions were pooled and concentrated to remove the volatiles. The remaining aqueous phase was adjusted to pH 6 with sat aq. NaHCO$_3$, then extracted with DCM (3×). The DCM extracts were washed with brine, dried (MgSO$_4$) and concentrated to give a glassy residue, which was lyophilized in CH$_3$CN/water to give a dark colored lyophilate (30.5 mg). HPLC and LC-MS showed the product was a diastereomeric mixture with a major diastereomer (88%) and a minor (12%).

The diastereomeric mixture was further purified by prep HPLC (Column: Lux Cellullose-4, 21×250 mm, 5μ; Mobile Phase: 20% IPA/0.1% formic acid/80% CO$_2$). The fraction of a front running peak (major diastereomer) was concentrated to dryness. The residue was partitioned between DCM and water, adjusted to pH 6 with sat. aq. NaHCO$_3$ solution. The DCM extracts were washed with brine, dried (MgSO$_4$) and concentrated. The obtained residue was lyophilized in CH$_3$CN/water to afford the desired product 2-((2S,3S,4R)-1-(5-(((3R,4R)-1-(5-ethoxy-2-fluorophenyl)-3-methylpiperidin-4-yl)oxy)pyrazin-2-yl)-4-(3-methoxypropoxy)-3-methylpyrrolidin-2-yl)acetic acid (19.97 mg). LC-MS Anal. Calc'd for $C_{29}H_{41}FN_4O_6$: 560.301, found [M+H] 561.4. $^1$H NMR (400 MHz, CDCl$_3$) δ 7.74 (d, J=1.3 Hz, 1H), 7.38 (d, J=1.1 Hz, 1H), 6.84 (dd, J=12.1, 8.8 Hz, 1H), 6.45 (dd, J=7.4, 3.0 Hz, 1H), 6.32 (dt, J=8.8, 3.2 Hz, 1H), 4.60-4.42 (m, 1H), 3.91 (q, J=6.9 Hz, 3H), 3.74-3.65 (m, 1H), 3.59-3.32 (m, 8H), 3.26 (s, 3H), 2.91 (dd, J=16.3, 3.5 Hz, 1H), 2.85-2.69 (m, 2H), 2.50 (dd, J=12.0, 10.2 Hz, 1H), 2.38 (d, J=7.3 Hz, 1H), 2.22-1.99 (m, 2H), 1.87-1.64 (m, 4H), 1.33 (t, J=6.9 Hz, 3H), 1.02-0.90 (m, 6H). hGPR40 EC$_{50}$=45 nM.

Example 5

2-(1-(5-(((3R,4R)-1-(5-Ethoxy-2-fluorophenyl)-3-methylpiperidin-4-yl)oxy)pyrazin-2-yl)-4-(3-methoxypropoxy)-3-methylpyrrolidin-2-yl)acetic acid

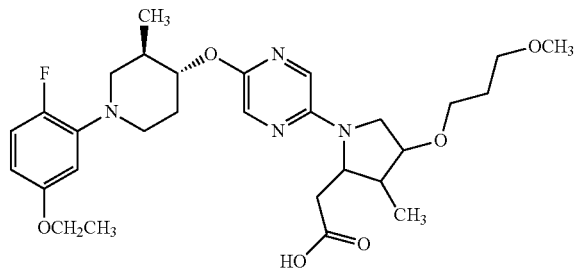 [SMILES: CCOc1ccc(F)c(N2CC[C@@H](Oc3cnc(N4CC(OCCCOC)C(C)C4CC(=O)O)cn3)[C@H](C)C2)c1]

The diastereomeric mixture obtained in Example 4 was further purified by prep HPLC (Column: Lux Cellullose-4, 21×250 mm, 5µ; Mobile Phase: 20% IPA/0.1% formic acid/80% CO$_2$). The fraction of a latter running peak (minor diastereomer) was concentrated to dryness. The residue was partitioned between DCM and water, adjusted to pH 6 with sat. aq. NaHCO$_3$ solution. The DCM extracts were washed with brine, dried (MgSO$_4$) and concentrated. The obtained residue was lyophilized in CH$_3$CN/water to afford 2-(1-(5-(((3R,4R)-1-(5-ethoxy-2-fluorophenyl)-3-methylpiperidin-4-yl)oxy)pyrazin-2-yl)-4-(3-methoxypropoxy)-3-methylpyrrolidin-2-yl)acetic acid (2.25 mg) as an off-white lyophilate. LC-MS Anal. Calc'd for C$_{29}$H$_{41}$FN$_4$O$_6$: 560.301, found [M+H] 561.4. $^1$H NMR (400 MHz, CDCl$_3$) δ 7.69 (s, 1H), 7.70 (s, 1H), 7.43 (s, 1H), 6.84 (dd, J=12.1, 8.8 Hz, 1H), 6.45 (dd, J=7.4, 3.0 Hz, 1H), 6.32 (dt, J=8.8, 3.1 Hz, 1H), 4.51 (d, J=4.4 Hz, 1H), 4.29 (d, J=3.5 Hz, 1H), 3.91 (q, J=6.9 Hz, 2H), 3.76-3.68 (m, 2H), 3.52 (td, J=6.3, 1.2 Hz, 2H), 3.44-3.31 (m, 4H), 3.25 (s, 3H), 3.12 (d, J=4.4 Hz, 1H), 2.78 (d, J=2.4 Hz, 1H), 2.69-2.33 (m, 4H), 2.22-2.04 (m, 2H), 1.77 (quin, J=6.3 Hz, 2H), 1.50 (br. s., 1H), 1.33 (t, J=6.9 Hz, 3H), 1.07 (d, J=7.0 Hz, 3H), 0.97 (d, J=6.6 Hz, 3H). hGPR40 EC$_{50}$=837 nM.

Example 6

2-((2R,4R)-1-(5-(((3R,4R)-1-(5-Chloro-2-methoxy-pyridin-4-yl)-3-methylpiperidin-4-yloxy)pyrazin-2-yl)-4-methoxypyrrolidin-2-yl)acetic acid

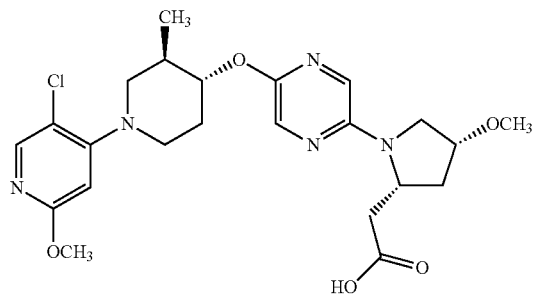 [SMILES: COc1cc(N2CC[C@@H](Oc3cnc(N4C[C@H](OC)C[C@@H]4CC(=O)O)cn3)[C@H](C)C2)c(Cl)cn1]

6A. (2R,4R)-tert-Butyl 2-(hydroxymethyl)-4-methoxy-pyrrolidine-1-carboxylate: A suspension of ((2R,4R)-4-methoxypyrrolidin-2-yl)methanol, hydrochloride salt (PCT/US2013/070213 filed Nov. 15, 2013) (1 g, 5.97 mmol), di-tert-butyl carbonate (1.953 g, 8.95 mmol) and sodium bicarbonate (1.503 g, 17.90 mmol) in THF (15 mL) and water (15 mL) was vigorously stirred at rt for 16 h. The reaction mixture was extracted with EtOAc (3×). The combined extracts were washed with brine, dried (Na$_2$SO$_4$) and concentrated. The crude product was purified by flash chromatography eluting with EtOAc/hexanes (0 to 50% gradient) to afford (2R,4R)-tert-butyl 2-(hydroxymethyl)-4-methoxypyrrolidine-1-carboxylate (1.3 g, 5.62 mmol, 94% yield) as a colorless oil. LC-MS Anal. Calc'd for C$_{11}$H$_{21}$NO$_4$: 231.147, found [M+H] 232.0.

6B. (2S,4R)-tert-Butyl 2-(cyanomethyl)-4-methoxypyrrolidine-1-carboxylate: To a solution of 6A (1.3 g, 5.62 mmol) in CH$_2$Cl$_2$ (25 mL) cooled to 0° C. was added Et$_3$N (1.567 mL, 11.24 mmol), followed by dropwise addition of methanesulfonyl chloride (0.653 mL, 8.43 mmol). After addition, the reaction was stirred at 0° C. for 40 min. TLC and LC-MS showed the reaction was complete. The reaction was diluted with CH$_2$Cl$_2$ and washed with 1N aq. HCl, sat. aq. NaHCO$_3$, brine, dried (MgSO$_4$) and concentrated. The obtained residue was dried in high vacuum to afford the desired product (2R,4R)-tert-butyl 4-methoxy-2-(((methylsulfonyl)oxy)methyl)pyrrolidine-1-carboxylate (1.65 g, 5.33 mmol, 95% yield) was immediately used for the reaction described below.

The obtained mesylate was dissolved in anhydrous DMSO (20 mL). NaCN (1.045 g, 21.33 mmol) was added to the solution. The resulting mixture was stirred at 50° C. for 16 h. LC-MS showed the reaction was complete. After cooling to rt, the reaction was quenched with water and extracted with EtOAc (3×). The combined extracts were washed with water, brine, dried (MgSO$_4$) and concentrated to dryness. The crude product was purified by flash chromatography eluting with EtOAc/hexanes (0-50% gradient). The desired fractions were pooled, concentrated and dried in high vacuum to afford the desired product (2S,4R)-tert-butyl 2-(cyanomethyl)-4-methoxypyrrolidine-1-carboxylate (1 g, 4.16 mmol, 78% yield) as a white foam. LC-MS Anal. Calc'd for C$_{12}$H$_{20}$N$_2$O$_3$: 240.147, found [M+H] 241.0.

6C. 2-((2S,4R)-4-Methoxypyrrolidin-2-yl)acetonitrile, hydrochloride salt: To a solution of 6B in dioxane (4 mL) was added 4 N HCl in dioxane (4 ml, 132 mmol). The reaction mixture was stirred at rt for 2 h. LC-MS and TLC showed the reaction was complete. The reaction was concentrated to give the desired product as a white solid, which was triturated with hexane. The solid was filtered and washed with hexane to afford 2-((2S,4R)-4-methoxypyrrolidin-2-yl)acetonitrile, hydrochloride salt (0.65 g, 3.68 mmol, 88% yield) as a white solid. LC-MS Anal. Calc'd for C$_7$H$_{12}$N$_2$O: 140.095, found [M+H] 141.1.

6D. 2-((4R)-1-(5-(((3R,4R)-1-(5-Chloro-2-methoxypyridin-4-yl)-3-methylpiperidin-4-yl)oxy)pyrazin-2-yl)-4-methoxypyrrolidin-2-yl)acetonitrile: To a microwave vial containing 1C (53 mg, 0.144 mmol) was added 6C (27.9 mg, 0.158 mmol), followed by 1,1'-bis(di-tert-butylphosphino) ferrocene (136 mg, 0.287 mmol), palladium(II) acetate (3.22 mg, 0.014 mmol), sodium tert-butoxide (48.3 mg, 0.502 mmol) and dioxane (1 mL). The reaction mixture was bubbled by a stream of argon for 1 min, then the vial was sealed and heated at 100° C. for 1 h under microwave irradiation. LC-MS showed the desired product formed. The reaction mixture was diluted with water, extracted with DCM (3×). The combined extracts were washed with brine, dried (MgSO$_4$) and concentrated to give a dark oily residue. The crude product was purified by flash chromatography eluting with EtOAc/hexanes (0-30%, 20 min; 30%, 5 min; 30-50%, 10 min). The desired fractions were pooled, concentrated and dried in high vacuum to afford 2-((4R)-1-(5-(((3R,4R)-1-(5-chloro-2-methoxypyridin-4-yl)-3-methylpiperidin-4-yl)oxy)pyrazin-2-yl)-4-methoxypyrrolidin-2-yl)acetonitrile (40 mg, 0.082 mmol, 57.2% yield) as an off-white foam, which contained about 20% of the other diastereomer). LC-MS Anal. Calc'd for $C_{23}H_{29}ClN_6O_3$: 472.199, found [M+H] 473.1 and 475.1.

Example 6: To a microwave vial containing 6D (40 mg, 0.085 mmol) was added EtOH (0.4 mL) and 6 M aqueous solution of KOH (0.28 mL, 1.69 mmol). The reaction vial was sealed and stirred at 120° C. for 2.5 h, LC-MS showed the reaction was complete. After cooling to rt, the reaction was concentrated to remove the volatiles. The remaining aqueous phase was adjusted to pH 6 with 1 N aq. HCl. The resulting suspension was diluted with water and extracted with DCM (3×). The combined extracts were washed with brine, dried (MgSO$_4$) and concentrated to dryness. The crude product was purified by prep HPLC (0.1% TFA-MeOH—H$_2$O) (PHENOMENEX® Luna Axia 5µ 30×100, gradient 50-90% over 12 min, hold at 90% for 3 min). Two diastereomers were separated well. The fractions of a latter running peak were pooled and concentrated to give a light yellow aqueous solution, which was transferred to a vial, CH$_3$CN added in, frozen and lyophilized to give an oily brownish residue. HPLC check showed the lyophilized product was about 85% pure. The product was purified again by prep HPLC (0.1% TFA-MeOH—H$_0$O) (PHENOMENEX® Luna Axia 5µ 30×100, gradient 50-90% over 12 min, hold at 90% for 3 min). The desired fractions were concentrated to remove the volatiles. The remaining aqueous was adjusted to pH 6 with sat. aq. NaHCO$_3$, then extracted with DCM (3×). The combined DCM extracts were washed with brine, dried (MgSO$_4$) and concentrated. The residue was lyophilized in CH$_3$CN/water to afford the desired product 2-((2R,4R)-1-(5-(((3R,4R)-1-(5-chloro-2-methoxypyridin-4-yl)-3-methylpiperidin-4-yl)oxy)pyrazin-2-yl)-4-methoxypyrrolidin-2-yl)acetic acid (3.97 mg, 7.99 µmol, 9.45% yield) as an off-white lyophilate. LC-MS Anal. Calc'd for $C_{23}H_{30}ClN_5O_5$: 491.194, found [M+H] 492.15. $^1$H NMR (400 MHz, CDCl$_3$) δ 7.91 (s, 1H), 7.74 (d, J=1.5 Hz, 1H), 7.39 (d, J=1.3 Hz, 1H), 6.21 (s, 1H), 4.55 (td, J=9.1, 4.4 Hz, 1H), 4.37-4.25 (m, 1H), 4.06 (br. s., 1H), 3.82 (s, 3H), 3.58-3.35 (m, 4H), 3.31 (s, 3H), 2.97 (dd, J=16.1, 3.5 Hz, 1H), 2.88-2.78 (m, 1H), 2.68 (dd, J=16.2, 8.3 Hz, 1H), 2.56 (dd, J=12.2, 9.8 Hz, 1H), 2.21-2.02 (m, 4H), 1.74 (d, J=10.6 Hz, 1H), 1.62-1.38 (m, 1H), 0.99 (d, J=6.6 Hz, 3H). hGPR40 EC$_{50}$=150 nM. hGPR40 IP1 EC$_{50}$=44 nM.

Example 7

2-((2S,4R)-1-(5-(((3R,4R)-1-(5-Chloro-2-methoxypyridin-4-yl)-3-methylpiperidin-4-yloxy)pyrazin-2-yl)-4-methoxypyrrolidin-2-yl)acetic acid

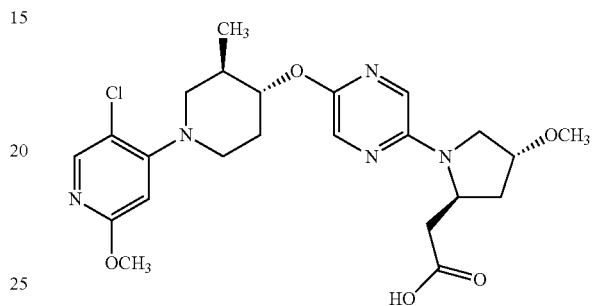

A diastereomeric mixture generated in Example 6 was separated by prep HPLC (0.1% TFA-MeOH—H$_2$O) (PHENOMENEX® Luna Axia 5µ 30×100, gradient 50-90% over 12 min, hold at 90% for 3 min). The fractions of a front running peak were pooled and concentrated to give a yellow aqueous solution, which was transferred to a vial and CH$_3$CN was added in. The mixture was frozen and lyophilized to give an oily residue. HPLC showed the lyophilized sample was about 89% pure. The product was purified again by prep HPLC (the same conditions as described above). The desired fraction was concentrated to remove the volatiles. The remaining aqueous was adjusted to pH 6 with sat. aq. NaHCO$_3$ and extracted with DCM (3×). The combined DCM extracts were washed with brine, dried (MgSO$_4$) and concentrated to dryness. The residue was lyophilized in CH$_3$CN/water to give 2-((2S,4R)-1-(5-(((3R,4R)-1-(5-chloro-2-methoxypyridin-4-yl)-3-methylpiperidin-4-yl)oxy)pyrazin-2-yl)-4-methoxypyrrolidin-2-yl)acetic acid (2.95 mg, 5.82 µmol, 6.88% yield). LC-MS Anal. Calc'd for $C_{23}H_{30}ClN_5O_5$: 491.194, found [M+H] 492.1. $^1$H NMR (400 MHz, CDCl$_3$) δ0 7.91 (s, 1H), 7.72 (d, J=1.1 Hz, 1H), 7.43 (d, J=1.3 Hz, 1H), 6.21 (s, 1H), 4.56 (td, J=9.2, 4.3 Hz, 1H), 4.31 (dd, J=7.0, 3.3 Hz, 1H), 4.10-4.00 (m, 1H), 3.82 (s, 3H), 3.66 (dd, J=10.3, 5.1 Hz, 1H), 3.48 (d, J=12.1 Hz, 2H), 3.35 (dd, J=10.2, 3.0 Hz, 1H), 3.29-3.22 (m, 3H), 2.96 (dd, J=15.7, 3.4 Hz, 1H), 2.87-2.78 (m, 1H), 2.61-2.40 (m, 2H), 2.38-2.28 (m, 1H), 2.24-2.05 (m, 2H), 2.04-1.95 (m, 1H), 1.84-1.67 (m, 1H), 1.60-1.38 (m, 1H), 0.99 (d, J=6.8 Hz, 3H). hGPR40 EC$_{50}$=3233 nM.

Example 8

2-((2S,4R)-1-(5-((3R,4R)-1-(5-Chloro-2-methoxy-pyridin-4-yl)-3-methylpiperidin-4-yloxy)pyrazin-2-yl)-4-(trifluoromethyl)pyrrolidin-2-yl)acetic acid

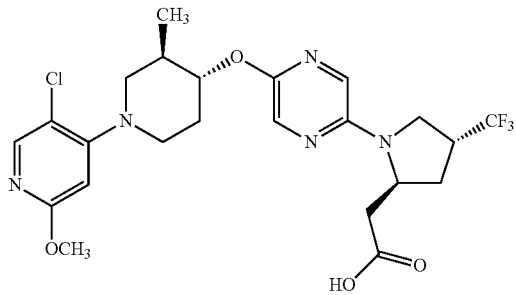 [SMILES: COc1cc(N2CC[C@@H](Oc3cnc(N4C[C@H](C(F)(F)F)C[C@H]4CC(=O)O)cn3)[C@H](C)C2)c(Cl)cn1]

8A. (2R,4R)-Benzyl 2-(hydroxymethyl)-4-(trifluoromethyl)pyrrolidine-1-carboxylate: To a stirring suspension of ((2R,4R)-4-(trifluoromethyl)pyrrolidin-2-yl)methanol, (1S)(+) 10-camphorsulfonic acid salt (PCT/US2013/070213 filed Nov. 15, 2013) (500 mg, 1.246 mmol) and sodium bicarbonate (220 mg, 2.62 mmol) in $CH_2Cl_2$ (3 mL) and water (3 mL) at rt was added benzyl carbonochloridate (0.187 mL, 1.308 mmol) dropwise over 5 min. After addition, the mixture was stirred at rt for 1.5 h. LC-MS showed the reaction was not complete. Additional amount of benzyl chloroformate (0.2 mL) was added and the reaction was allowed to stir for additional 30 min. The reaction was quenched by addition of water and the mixture extracted with EtOAc (3×). The combined extracts were washed with water and brine, dried ($MgSO_4$) and concentrated. The crude product was purified by flash chromatography eluting with hexane/EtOAc (0%-50%, 20 min; 50%, 10 min). The desired fractions were pooled, concentrated and dried in vacuum to afford the desired product (2R,4R)-benzyl 2-(hydroxymethyl)-4-(trifluoromethyl)pyrrolidine-1-carboxylate (370 mg, 1.208 mmol, 97% yield) as a colorless oil. LC-MS Anal. Calc'd for $C_{14}H_{16}F_3NO_3$: 303.108, found [M+H] 304.5.

8B. (2R,4R)-Benzyl 2-(cyanomethyl)-4-(trifluoromethyl)pyrrolidine-1-carboxylate: To a stirring solution of 8A (370 mg, 1.220 mmol) in $CH_2Cl_2$ (6 mL) cooled at 0° C. was added $Et_3N$ (0.340 mL, 2.440 mmol), followed by methanesulfonyl chloride (0.143 mL, 1.830 mmol) dropwise over 3 min. After addition, the resulting cloudy solution was stirred at 0° C. for 60 min. LC-MS showed the desired product formed. The reaction mixture was diluted with EtOAc, washed with water (2×), sat. aq. $NaHCO_3$, brine, dried ($MgSO_4$) and concentrated to dryness. The obtained oily residue was dried in high vacuum to afford (2R,4R)-benzyl 2-(((methylsulfonyl)oxy)methyl)-4-(trifluoromethyl)pyrrolidine-1-carboxylate as an oily residue, which was used immediately in the reaction described below.

The obtained mesylate was dissolved in anhydrous DMSO (5 mL), NaCN (239 mg, 4.88 mmol) was added. The resulting mixture was stirred at 50° C. for 16 h. LC-MS showed the reaction was complete. After cooling to rt, the reaction was quenched with water and extracted with EtOAc (3×). The combined extracts were washed with water (2×), brine, dried ($MgSO_4$) and concentrated to dryness. The crude product was purified by flash chromatography eluting with EtOAc/hexanes (0-40%, 20 min; 40%, 10 min) to afford the desired product (2R,4R)-benzyl 2-(cyanomethyl)-4-(trifluoromethyl) pyrrolidine-1-carboxylate (96 mg, 0.271 mmol, 22.17% yield) as an oily residue. LC-MS Anal. Calc'd for $C_{15}H_{15}F_3N_2O_2$: 312.109, found [M+H] 313.1. $^1$H NMR (400 MHz, $CDCl_3$) δ 7.39-7.22 (m, 5H), 5.17-4.98 (m, 2H), 4.12-4.00 (m, 1H), 3.88 (d, J=8.4 Hz, 1H), 3.42 (t, J=10.6 Hz, 1H), 3.01-2.76 (m, 3H), 2.54-2.39 (m, 1H), 2.10-1.96 (m, 1H).

8C. 2-((2R,4R)-4-(Trifluoromethyl)pyrrolidin-2-yl)acetonitrile: To a solution of 8B (95 mg, 0.304 mmol) in EtOAc (5 mL) was added Pd/C (32.4 mg, 0.015 mmol) (5% dry basis, Degussa type). After purging with hydrogen (3×), the suspension was vigorously stirred at rt under a hydrogen balloon for 16 h. LC-MS showed the reaction was complete. The mixture was filtered and the catalyst washed with EtOAc. The combined filtrate was concentrated to dryness. The obtained residue was dried in high vacuum for 30 min to afford 2-((2R,4R)-4-(trifluoromethyl)pyrrolidin-2-yl)acetonitrile (90 mg, 0.505 mmol) (containing unknown impurities) as an oily residue. LC-MS Anal. Calc'd for $C_7H_9F_3N_2$: 178.072, found [M+H] 179.1.

8D. 2-((4R)-1-(5-((3R,4R)-1-(5-Chloro-2-methoxypyridin-4-yl)-3-methylpiperidin-4-yloxy)pyrazin-2-yl)-4-(trifluoromethyl)pyrrolidin-2-yl)acetonitrile: To a microwave vial containing 1C (60 mg, 0.162 mmol) was added 1,1'-bis(di-tert-butylphosphino)ferrocene (154 mg, 0.325 mmol), palladium(II) acetate (3.65 mg, 0.016 mmol) and a solution of 8C (34.7 mg, 0.195 mmol) in dioxane (0.7 mL), followed by sodium tert-butoxide (39.0 mg, 0.406 mmol). The mixture was bubbled with a stream of argon for 1 min, then the vial was sealed and heated at 100° C. for 1 h under microwave irradiation. LC-MS showed the reaction was complete and the desired product formed. The reaction mixture was cooled to rt and diluted with water, extracted with DCM (3×). The combined extracts were washed with brine, dried ($MgSO_4$) and concentrated to give a dark oily residue. The crude product was purified by flash chromatography eluting with EtOAc/hexanes (0-30%, 20 min; 30%, 5 min; 30-50%, 10 min). The desired fractions were pooled, concentrated and dried in high vacuum to afford 2-((4R)-1-(5-(3R,4R)-1-(5-chloro-2-methoxypyridin-4-yl)-3-methylpiperidin-4-yl)oxy)pyrazin-2-yl)-4-(trifluoromethyl)pyrrolidin-2-yl)acetonitrile (60 mg, 0.113 mmol, 69.4% yield) as an off-white foam which contained two diastereomers in a ratio of 3:1). LC-MS Anal. Calc'd for $C_{23}H_{26}ClF_3N_6O_2$: 510.176, found [M+H] 511.5 and 513.5.

Example 8: To a microwave vial containing a diastereomeric mixture of 8D (60 mg, 0.117 mmol) was added EtOH (0.8 mL) and 6 M aqueous solution of KOH (0.39 mL, 2.349 mmol). The reaction was sealed and stirred at 120° C. for 2.5 h, LC-MS showed the reaction was complete. After cooling to rt, the reaction mixture was concentrated to remove the volatile. The remaining aqueous phase was adjusted to pH 6 with 1 N aq. HCl. The resulting suspension was diluted with water and extracted with DCM (3×). The combined extracts were washed with brine, dried ($MgSO_4$) and concentrated to dryness. The crude product was purified by prep HPLC (0.1% TFA-MeOH—$H_2O$) (PHENOMENEX® Luna Axia 5μ 30×100, gradient 60-95% over 15 min, hold at 95% for 3 min). Two diastereomers were separated. The fractions of a latter running peak were pooled and concentrated. The remaining aqueous phase was adjusted to pH 6 with sat. aq. $NaHCO_3$ and extracted with DCM (3×). The combined extracts were washed with brine, dried ($MgSO_4$) and concentrated. The obtained residue was lyophilized in $CH_3CN$/water to afford 2-((2R,4R)-1-(5-(((3R,4R)-1-(5-chloro-2-methoxypyridin-4-yl)-3-methylpiperidin-4-yl)oxy)pyrazin- 2-yl)-4-(trifluoromethyl)pyrrolidin-2-yl)acetic acid (the major diastereomer) (22.45 mg, 0.040 mmol, 34.3% yield) as a gray colored lyophilate. LC-MS Anal. Calc'd for $C_{23}H_{27}ClF_3N_5O_4$: 529.17, found [M+H] 530.15. $^1$H NMR (400 MHz, CDCl$_3$) δ 7.91 (s, 1H), 7.78 (d, J=1.5 Hz, 1H), 7.37 (d, J=1.3 Hz, 1H), 6.21 (s, 1H), 4.58 (td, J=9.1, 4.2 Hz, 1H), 4.48 (t, J=8.6 Hz, 1H), 3.82 (s, 3H), 3.69-3.60 (m, 1H), 3.52-3.34 (m, 3H), 3.16 (dd, J=17.6, 8.1 Hz, 1H), 2.97-2.77 (m, 2H), 2.56 (dd, J=12.3, 9.7 Hz, 1H), 2.45-2.25 (m, 2H), 2.22-2.00 (m, 4H), 1.73 (dd, J=13.0, 2.4 Hz, 1H), 0.99 (d, J=6.6 Hz, 3H). hGPR40 EC$_{50}$=955 nM.

Example 9

2-((2R,4R)-1-(5-(((3R,4R)-1-(5-Chloro-2-methoxy-pyridin-4-yl)-3-methylpiperidin-4-yloxy)pyrazin-2-yl)-4-(trifluoromethyl)pyrrolidin-2-yl)acetic acid

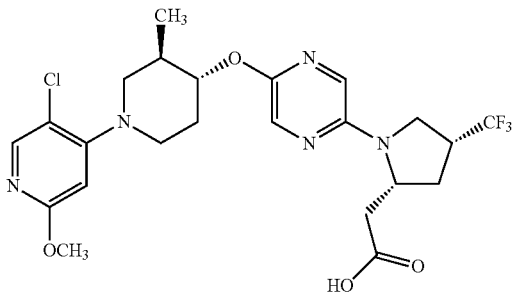 [SMILES: COc1cc(N2CC[C@@H](Oc3cnc(N4C[C@H](C(F)(F)F)C[C@@H]4CC(=O)O)cn3)[C@H](C)C2)c(Cl)cn1]

A mixture of the two diastereomers in Example 8 was separated by prep HPLC (0.1% TFA-MeOH—H$_2$O) (PHENOMENEX® Luna Axia 5μ 30×100, gradient 60-95% over 15 min, hold at 95% for 3 min). The fractions of a front running peak were pooled and concentrated. The remaining aqueous phase was adjusted to pH 6 with sat. aq. NaHCO$_3$ and extracted with DCM (3×). The combined extracts were washed with brine, dried (MgSO$_4$) and concentrated. The obtained residue was lyophilized in CH$_3$CN/water to afford 2-((2R,4R)-1-(5-(((3R,4R)-1-(5-chloro-2-methoxypyridin-4-yl)-3-methylpiperidin-4-yl)oxy)pyrazin-2-yl)-4-(trifluoromethyl)pyrrolidin-2-yl)acetic acid (5.28 mg, 9.86 μmol, 8.40% yield) as an off-white lyophilate. LC-MS Anal. Calc'd for $C_{23}H_{27}ClF_3N_5O_4$: 529.17, found [M+H] 530.15. $^1$H NMR (400 MHz, CDCl$_3$) δ 7.91 (s, 1H), 7.76 (d, J=1.5 Hz, 1H), 7.41 (d, J=1.3 Hz, 1H), 6.21 (s, 1H), 4.59 (td, J=9.2, 4.4 Hz, 1H), 4.33 (dd, J=7.7, 2.9 Hz, 1H), 3.82 (s, 3H), 3.67-3.53 (m, 2H), 3.48 (dd, J=12.2, 1.9 Hz, 2H), 3.13 (dd, J=16.1, 3.3 Hz, 1H), 3.01-2.89 (m, 1H), 2.89-2.78 (m, 1H), 2.66-2.51 (m, 2H), 2.45 (dd, J=16.2, 8.5 Hz, 1H), 2.23-1.95 (m, 4H), 1.81-1.68 (m, 1H), 0.99 (d, J=6.6 Hz, 3H). hGPR40 EC$_{50}$=84 nM.

What is claimed is:
1. A compound of Formula (I):

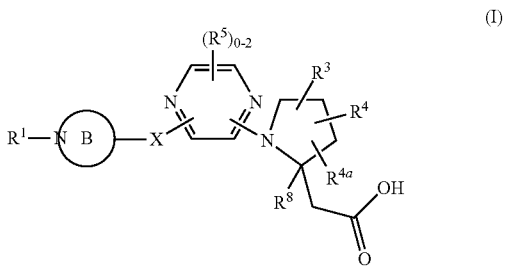

or a stereoisomer, a tautomer, a pharmaceutically acceptable salt, or a solvate thereof, wherein:
X is independently selected from: a bond, O, S, NH, N(C$_{1-4}$ alkyl), CH$_2$, CH$_2$CH$_2$, CH(C$_{1-4}$ alkyl), OCH$_2$, CH$_2$O, OCH$_2$CH$_2$, and CH$_2$CH$_2$O;
ring B is independently a 4- to 7-membered saturated heterocycle containing carbon atoms, the nitrogen atom shown in the ring B and 0-1 additional heteroatom selected from N, O, and S; and ring B is substituted with 0-4 R$^2$;
R$^1$ is independently phenyl, benzyl, naphthyl or a 5- to 10-membered heteroaryl containing carbon atoms and 1-4 heteroatoms selected from N, NR$^{11}$, O, and S; wherein said phenyl, benzyl, naphthyl and heteroaryl are each substituted with 0-3 R$^6$;
R$^2$, at each occurrence, is independently selected from: =O, OH, halogen, C$_{1-6}$ alkyl substituted with 0-1 R$^{12}$, C$_{1-6}$ alkoxy substituted with 0-1 R$^{12}$, C$_{1-4}$ haloalkyl substituted with 0-1 R$^{12}$, C$_{1-4}$ haloalkoxy substituted with 0-1 R$^{12}$, —(CH$_2$)$_m$—C$_{3-6}$ carbocycle substituted with 0-1 R$^{12}$, and —(CH$_2$)$_m$-(5- to 10-membered heteroaryl containing carbon atoms and 1-4 heteroatoms selected from N, NR$^{11}$, O, and S); wherein said heteroaryl is substituted with 0-1 R$^{12}$;
when two R$^2$ groups are attached to two different carbon atoms, they may combine to form a 1- to 3-membered carbon atom bridge over ring B;
when two R$^2$ groups are attached to the same carbon, they may combine, together with the carbon atom to which they are attached, to form a 3- to 6-membered carbon atom containing spiro ring;
R$^3$ is independently selected from: H, halogen, CN, OH, CO$_2$H, C$_{1-6}$ alkyl substituted with 0-1 R$^{10}$, C$_{2-6}$ alkenyl substituted with 0-1 R$^{10}$, C$_{2-6}$ alkynyl substituted with 0-1 R$^{10}$, C$_{1-4}$ haloalkyl substituted with 0-1 R$^{10}$, C$_{1-6}$ haloalkoxy substituted with 0-1 R$^{10}$, —O(CH$_2$)$_{1-2}$O(CH$_2$)$_{1-4}$R$^{10}$, OR$^9$, SR$^9$, C(O)OR$^9$, CO$_2$R$^9$, S(O)R$^9$, SO$_2$R$^9$, CONHR$^9$, —(O)$_n$—(CH$_2$)$_m$-(phenyl substituted with 0-2 R$^{10}$), and —(O)$_n$—(CH$_2$)$_m$-(5- to 10-membered heteroaryl containing carbon atoms and 1-4 heteroatoms selected from N, NR$^{11}$, O, and S; wherein said heteroaryl is substituted with 0-2 R$^{10}$);
R$^4$ and R$^{4a}$ are independently selected from: H, halogen, C$_{1-6}$ alkyl, C$_{1-6}$ alkoxy, and —(CH$_2$)$_m$—C$_{3-6}$ carbocycle;
R$^5$, at each occurrence, is independently selected from: halogen, C$_{1-6}$ alkyl, C$_{1-6}$ alkoxy, C$_{1-6}$ haloalkyl, and C$_{1-6}$ haloalkoxy;

R⁶, at each occurrence, is independently selected from: halogen, OH, C₁₋₄ alkylthio, CN, SO₂(C₁₋₂ alkyl), N(C₁₋₄ alkyl)₂, C₁₋₄ haloalkyl, C₁₋₄ haloalkoxy, C₁₋₈ alkyl substituted with 0-1 R⁷, C₁₋₆ alkoxy substituted with 0-1 R⁷, —(O)ₙ—(CH₂)ₘ—(C₃₋₁₀ carbocycle substituted with 0-2 R⁷), and —(CH₂)ₘ-(5- to 10-membered heteroaryl containing carbon atoms and 1-4 heteroatoms selected from N, NR¹¹, O, and S); wherein said heteroaryl is substituted with 0-2 R⁷;

R⁷, at each occurrence, is independently selected from: halogen, OH, C₁₋₄ alkyl, C₂₋₄ alkenyl, C₁₋₄ alkoxy, C₁₋₄ alkylthio, C₁₋₄ haloalkyl, C₁₋₄ haloalkoxy, SCF₃, CN, NO₂, NH₂, NH(C₁₋₄ alkyl), N(C₁₋₄ alkyl)₂, SO₂(C₁₋₂ alkyl), and phenyl;

R⁸ is independently selected from: H and C₁₋₄ alkyl;

R⁹, at each occurrence, is independently selected from: C₁₋₆ alkyl substituted with 0-1 R¹⁰, and C₁₋₄ haloalkyl substituted with 0-1 R¹⁰;

R¹⁰, at each occurrence, is independently selected from: CN, C₁₋₄ alkoxy, C₁₋₄ haloalkoxy, CO₂(C₁₋₄ alkyl), SO₂(C₁₋₄ alkyl), and tetrazolyl;

R¹¹, at each occurrence, is independently selected from: H, C₁₋₄ alkyl and benzyl;

R¹², at each occurrence, is independently selected from: OH, halogen, CN, C₁₋₄ alkyl, C₁₋₄ alkoxy, C₁₋₄ haloalkyl, C₁₋₄ haloalkoxy, CO₂(C₁₋₄ alkyl), and tetrazolyl;

m, at each occurrence, is independently 0, 1, or 2; and n, at each occurrence, is independently 0 or 1.

2. A compound according to Formula I of claim 1, wherein R⁴ is hydrogen and R⁸ is hydrogen, further characterized by Formula (II):

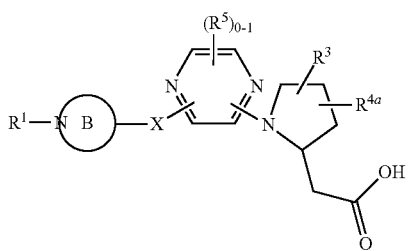

(II)

or a stereoisomer, a tautomer, a pharmaceutically acceptable salt, or a solvate thereof, wherein:

X is independently selected from: O, N(CH₃), CH₂, CH₂O, and CH₂CH₂O;

ring B is independently a 4- to 7-membered saturated heterocycle containing carbon atoms and the nitrogen atom shown in ring B; and ring B is substituted with 0-4 R²;

R¹ is independently phenyl, benzyl, naphthyl or a 5- to 10-membered heteroaryl containing carbon atoms and 1-4 heteroatoms selected from N, NR¹¹, O, and S; wherein said phenyl, benzyl, naphthyl and heteroaryl are each substituted with 0-3 R⁶;

R², at each occurrence, is independently selected from: =O, OH, halogen, C₁₋₄ alkyl substituted with 0-1 R¹², C₁₋₄ alkoxy substituted with 0-1 R¹², C₁₋₄ haloalkyl, C₁₋₄ haloalkoxy, and benzyl;

when two R² groups are attached to two different carbon atoms, they may combine to form a 1- to 3-membered carbon atom bridge over ring B;

when two R² groups are attached to the same carbon, they may combine, together with the carbon atom to which they are attached, to form a 3- to 6-membered carbon atom containing spiro ring;

R³ is independently selected from: C₁₋₆ alkyl substituted with 0-1 R¹⁰, C₁₋₆ alkoxy substituted with 0-1 R¹⁰, C₁₋₄ haloalkyl substituted with 0-1 R¹⁰, and C₁₋₄ haloalkoxy substituted with 0-1 R¹⁰, and —O(CH₂)₁₋₂O(CH₂)₁₋₄R¹⁰;

R⁴ᵃ is independently selected from: H, halogen, C₁₋₄ alkyl, C₁₋₄ alkoxy, and —(CH₂)ₘ—C₃₋₆ carbocycle;

R⁵, at each occurrence, is independently selected from: halogen, C₁₋₆ alkyl, C₁₋₆ haloalkyl, C₁₋₆ alkoxy, and C₁₋₆ haloalkoxy;

R⁶, at each occurrence, is independently selected from: halogen, OH, C₁₋₄ alkylthio, CN, SO₂(C₁₋₂ alkyl), N(C₁₋₄ alkyl)₂, C₁₋₄ haloalkyl, C₁₋₄ haloalkoxy, C₁₋₈ alkyl substituted with 0-1 R⁷, C₁₋₄ alkoxy substituted with 0-1 R⁷, —(O)ₙ—(CH₂)ₘ—(C₃₋₆ carbocycle substituted with 0-2 R⁷), —(CH₂)ₘ-(naphthyl substituted with 0-2 R⁷), and —(CH₂)ₘ-(5- to 10-membered heteroaryl containing carbon atoms and 1-4 heteroatoms selected from N, O, and S; wherein said heteroaryl is substituted with 0-2 R⁷);

R⁷, at each occurrence, is independently selected from: halogen, OH, C₁₋₄ alkyl, C₂₋₄ alkenyl, C₁₋₄ alkoxy, C₁₋₄ alkylthio, C₁₋₄ haloalkyl, C₁₋₄ haloalkoxy, SCF₃, CN, NO₂, NH₂, NH(C₁₋₄ alkyl), N(C₁₋₄ alkyl)₂, SO₂(C₁₋₂ alkyl), and phenyl;

R¹⁰, at each occurrence, is independently selected from: CN, C₁₋₄ alkoxy, C₁₋₄ haloalkoxy, CO₂(C₁₋₄ alkyl), SO₂(C₁₋₄ alkyl), and tetrazolyl;

R¹¹, at each occurrence, is independently selected from: H, C₁₋₄ alkyl and benzyl;

R¹², at each occurrence, is independently selected from: halogen, CN, C₁₋₄ alkyl, C₁₋₄ alkoxy, C₁₋₄ haloalkyl, C₁₋₄ haloalkoxy, CO₂(C₁₋₄ alkyl), and tetrazolyl;

m, at each occurrence, is independently 0, 1, or 2; and n, at each occurrence, is independently 0 or 1.

3. A compound of Formula (I) according the claim 1, or a stereoisomer, a tautomer, a pharmaceutically acceptable salt, or a solvate thereof, wherein:

ring B is independently selected from:

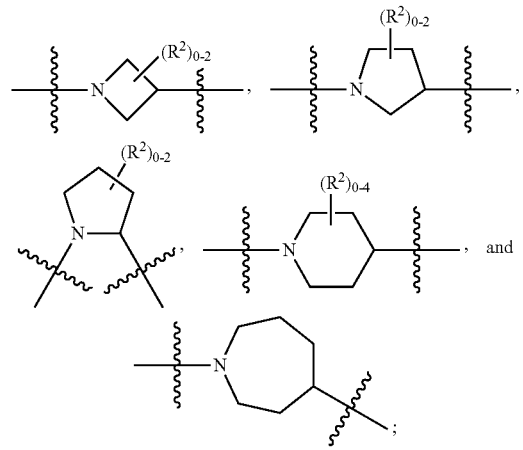

R¹ is independently phenyl substituted with 0-3 R⁶ or a heteroaryl substituted with 0-2 R⁶; wherein said heteroaryl is selected from: furanyl, oxazolyl, thiazolyl, pyrazolyl, oxadiazolyl, pyridinyl, pyrimidinyl, and pyrazinyl;

$R^2$, at each occurrence, is independently selected from: OH, halogen, $C_{1-4}$ alkyl substituted with 0-1 CN, $C_{1-4}$ alkoxy, benzyl, and tetrazolylmethyl;

$R^3$ is independently selected from: $C_{1-4}$ alkyl substituted with 0-1 $R^{10}$, $C_{1-4}$ alkoxy substituted with 0-1 $R^{10}$, $C_{1-4}$ haloalkyl substituted with 0-1 $R^{10}$, and $C_{1-4}$ haloalkoxy substituted with 0-1 $R^{10}$;

$R^{4a}$ is independently selected from: H, halogen $C_{1-4}$ alkyl, $C_{1-4}$ alkoxy, and $C_{3-6}$ cycloalkyl;

$R^6$, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl; and $R^{10}$, at each occurrence, is independently selected from: CN, $C_{1-4}$ alkoxy, $C_{1-4}$ haloalkoxy, $CO_2(C_{1-4}$ alkyl), and tetrazolyl.

4. A compound of Formula (I) according to claim 1, or a stereoisomer, a tautomer, a pharmaceutically acceptable salt, or a solvate thereof, wherein:

ring B is independently selected from:

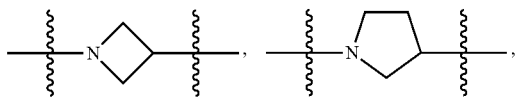

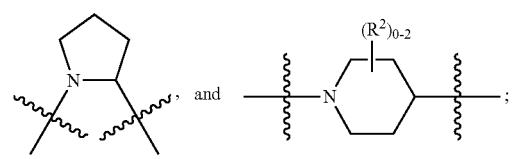

$R^1$, at each occurrence, is independently phenyl substituted with 0-3 $R^6$, pyridinyl substituted with 0-2 $R^6$, pyrazinyl substituted with 0-2 $R^6$, pyrimidinyl substituted with 0-2 $R^6$, or thiazolyl substituted with 0-2 $R^6$; and $R^2$, at each occurrence, is independently selected from: halogen, $C_{1-4}$ alkyl, $C_{1-4}$ alkoxy and tetrazolylmethyl.

5. A compound of Formula (I) according to claim 1, or a stereoisomer, a tautomer, a pharmaceutically acceptable salt, or a solvate thereof, wherein:

$R^1$, at each occurrence, is independently phenyl substituted with 0-3 $R^6$ or pyridinyl substituted with 0-2 $R^6$;

$R^3$, at each occurrence, is independently selected from: $C_{1-4}$ alkyl substituted with 0-1 $C_{1-4}$ alkoxy, $C_{1-4}$ alkoxy substituted with 0-1 $C_{1-4}$ alkoxy, and $C_{1-4}$ haloalkyl; and $R^6$, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl.

6. A compound of Formula (III) or (IIIa):

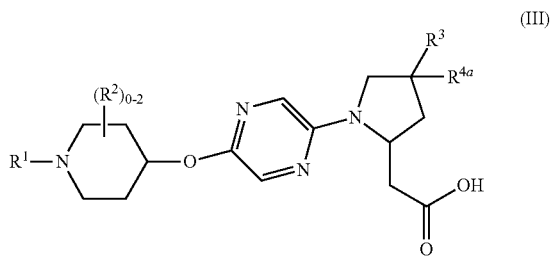

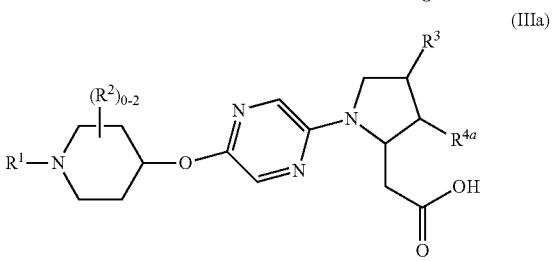

or a stereoisomer, a tautomer, a pharmaceutically acceptable salt, or a solvate thereof, wherein:

$R^1$, at each occurrence, is independently phenyl substituted with 0-3 $R^6$ or pyridinyl substituted with 0-2 $R^6$;

$R^2$, at each occurrence, is independently selected from: halogen, $C_{1-4}$ alkyl, and $C_{1-4}$ alkoxy;

$R^3$, at each occurrence, is independently: $C_{1-4}$ alkyl substituted with 0-1 $C_{1-4}$ alkoxy, $C_{1-4}$ alkoxy substituted with 0-1 $C_{1-4}$ alkoxy, and $C_{1-4}$ haloalkyl;

$R^{4a}$, at each occurrence, is independently selected from: H, halogen, $C_{1-4}$ alkyl, $C_{1-4}$ alkoxy, and cyclopropyl; and $R^6$, at each occurrence, is independently selected from: halogen, $C_{1-6}$ alkyl, $C_{1-4}$ alkoxy, $C_{3-6}$ cycloalkyl substituted with 0-2 $C_{1-4}$ alkyl, and $C_{5-6}$ cycloalkenyl substituted with 0-2 $C_{1-4}$ alkyl.

7. A pharmaceutical composition, comprising a pharmaceutically acceptable carrier and a compound of claim 1, or a stereoisomer, a tautomer, or a pharmaceutically acceptable salt or solvate thereof.

8. The pharmaceutical composition according to claim 7, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, and appetite suppressants.

9. The pharmaceutical composition according to claim 7, further comprising a dipeptidyl peptidase-IV inhibitor and/or a sodium-glucose transporter-2 inhibitor.

10. A compound according to claim 1, or a stereoisomer, a tautomer, or a pharmaceutically acceptable salt or solvate thereof, for use in modulating or treating diabetes, hyperglycemia, impaired glucose tolerance, gestational diabetes, insulin resistance, hyperinsulinemia, and diabetic kidney disease.

11. A compound for use according to claim 10, wherein the compound, or a stereoisomer, a tautomer, or a pharmaceutically acceptable salt or solvate thereof, is used simultaneously, separately or sequentially with one or more additional therapeutic agents.

12. A compound according to claim 1, having the structure:

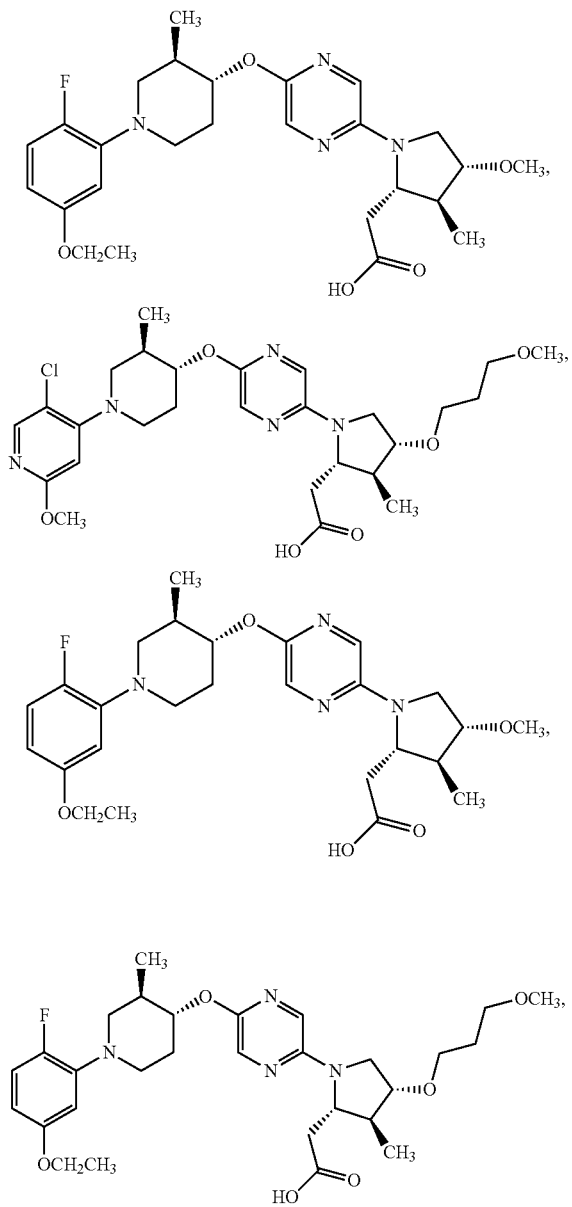
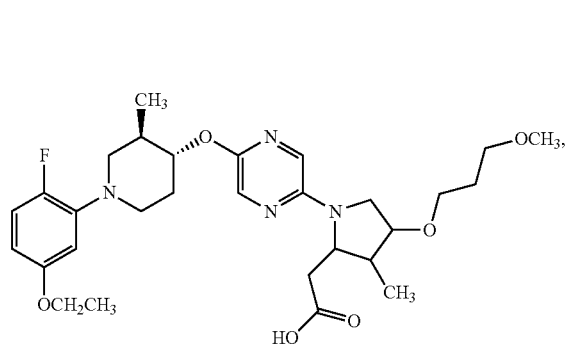
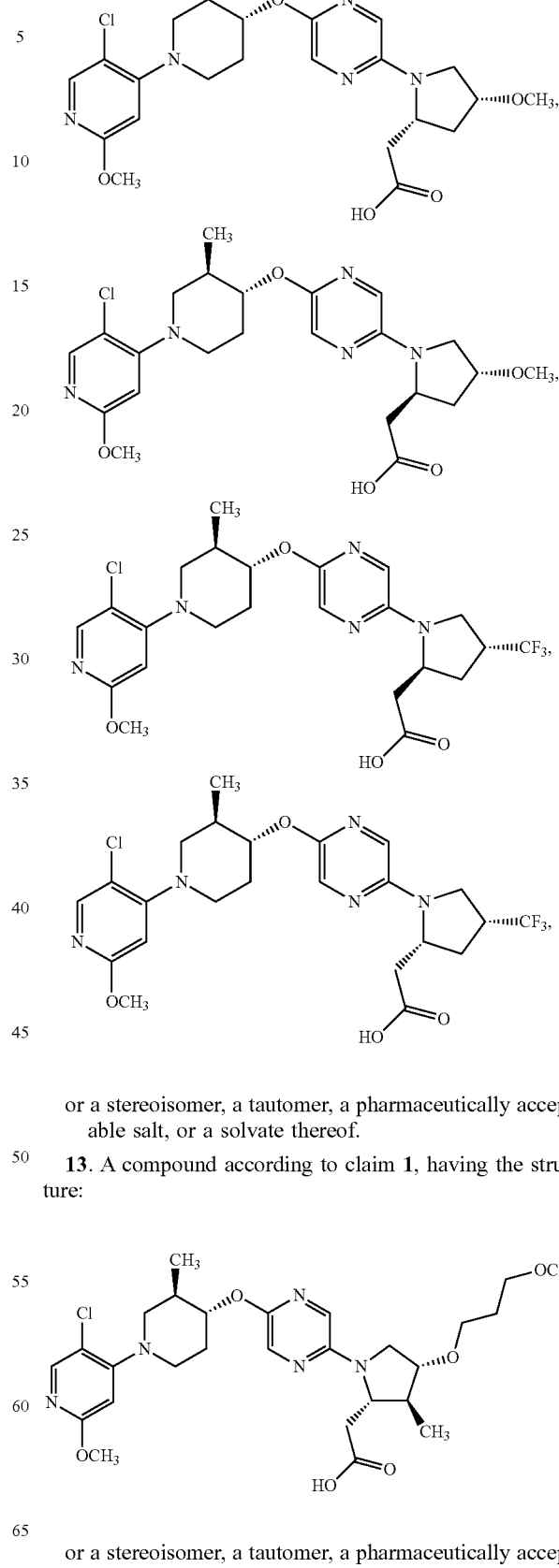

or a stereoisomer, a tautomer, a pharmaceutically acceptable salt, or a solvate thereof.

13. A compound according to claim 1, having the structure:

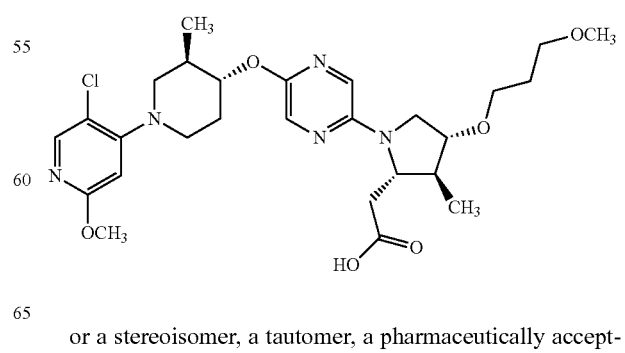

or a stereoisomer, a tautomer, a pharmaceutically acceptable salt, or a solvate thereof.

14. A compound according to claim 1, having the structure:

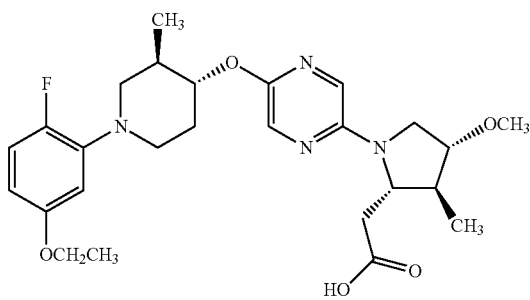 [SMILES: CCOc1ccc(F)c(N2CC[C@@H](Oc3cnc(N4C[C@H](OC)[C@@H](C)[C@@H]4CC(=O)O)cn3)[C@H](C)C2)c1]

or a stereoisomer, a tautomer, a pharmaceutically acceptable salt, or a solvate thereof.

15. A compound according to claim 1, having the structure:

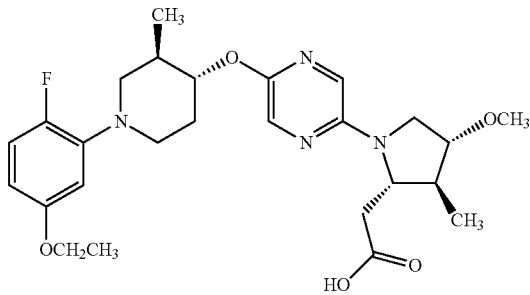 [SMILES: CCOc1ccc(F)c(N2CC[C@@H](Oc3cnc(N4C[C@H](OC)[C@@H](C)[C@@H]4CC(=O)O)cn3)[C@H](C)C2)c1]

or a stereoisomer, a tautomer, a pharmaceutically acceptable salt, or a solvate thereof.

16. A compound according to claim 1, having the structure:

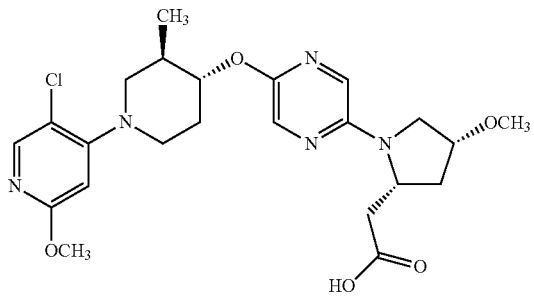 [SMILES: COc1cc(N2CC[C@@H](Oc3cnc(N4C[C@H](OC)C[C@@H]4CC(=O)O)cn3)[C@H](C)C2)c(Cl)cn1]

or a stereoisomer, a tautomer, a pharmaceutically acceptable salt, or a solvate thereof.

17. A compound according to claim 1, having the structure:

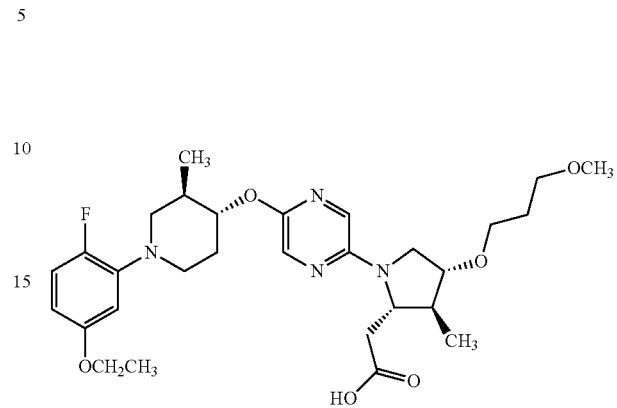

or a stereoisomer, a tautomer, a pharmaceutically acceptable salt, or a solvate thereof.

18. A compound according to claim 1, having the structure:

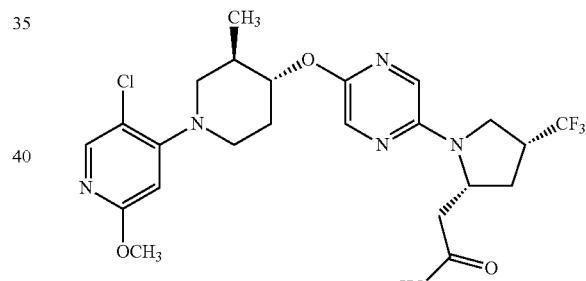

or a stereoisomer, a tautomer, a pharmaceutically acceptable salt, or a solvate thereof.

* * * * *